(12) United States Patent
Beiriger

(10) Patent No.: US 8,425,780 B2
(45) Date of Patent: Apr. 23, 2013

(54) DIALYSIS SYSTEM VENTING DEVICES AND RELATED SYSTEMS AND METHODS

(75) Inventor: Michael James Beiriger, Pittsburgh, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 473 days.

(21) Appl. No.: 12/722,061

(22) Filed: Mar. 11, 2010

(65) Prior Publication Data

US 2011/0220562 A1  Sep. 15, 2011

(51) Int. Cl.
*B01D 19/00* (2006.01)
*B01D 61/26* (2006.01)
*A61M 39/00* (2006.01)

(52) U.S. Cl.
USPC .......... 210/646; 95/266; 96/108; 96/182; 96/193; 210/85; 210/120; 210/188; 210/257.2; 210/258; 210/259; 210/321.6; 604/6.09

(58) Field of Classification Search .......... 210/85, 210/90, 96.2, 109, 110, 117, 120, 123, 136, 210/188, 257.2, 259, 321.6, 321.71, 645–647, 210/258, 436, 472; 604/4.01, 5.01, 6.01, 604/6.09, 65; 96/108, 155, 182, 193; 95/241, 95/266
See application file for complete search history.

(56) References Cited

U.S. PATENT DOCUMENTS

| | | | |
|---|---|---|---|
| 2,368,281 A * | 1/1945 | Wittenberg | 251/211 |
| 3,985,135 A | 10/1976 | Carpenter et al. | |
| 4,026,669 A | 5/1977 | Leonard et al. | |
| 4,054,522 A | 10/1977 | Pinkerton | |
| 4,370,983 A | 2/1983 | Lichtenstein | |
| 4,436,620 A | 3/1984 | Bellotti et al. | |
| 4,479,762 A | 10/1984 | Bilstad et al. | |
| 4,536,201 A * | 8/1985 | Brorsson et al. | 96/167 |
| 4,643,713 A | 2/1987 | Viitala | |
| 4,662,906 A | 5/1987 | Matkovich et al. | |
| 4,840,546 A * | 6/1989 | Nass | 417/403 |
| 4,927,411 A | 5/1990 | Pastrone et al. | |
| 4,997,464 A | 3/1991 | Kopf | |
| 5,061,236 A | 10/1991 | Sutherland et al. | |

(Continued)

FOREIGN PATENT DOCUMENTS

| | | |
|---|---|---|
| DE | 198 37 667 | 3/2000 |
| DE | 100 42 324 | 2/2002 |

(Continued)

OTHER PUBLICATIONS

Gambro®, "DEHP-free cartridge blood sets,"© Nov. 2004, Gambro, Inc., Lakewood, CO, 4 pp.

(Continued)

*Primary Examiner* — Joseph Drodge
(74) *Attorney, Agent, or Firm* — Fish & Richardson P.C.

(57) ABSTRACT

This disclosure relates to dialysis venting devices and related methods. In some aspects, a dialysis system includes a fluid inlet line, a venting device in fluid communication with the fluid inlet line, and a fluid outlet line in fluid communication with the venting device. The venting device can include a housing defining a fluid chamber, a valve member disposed above the fluid chamber between a lower seat and an upper seat, and a pump that is operable to draw fluid into the fluid chamber from the fluid inlet line and to force fluid out of the fluid chamber into the fluid outlet line.

34 Claims, 12 Drawing Sheets

U.S. PATENT DOCUMENTS

| | | | |
|---|---|---|---|
| 5,186,431 A * | 2/1993 | Tamari | 251/5 |
| 5,330,425 A | 7/1994 | Utterberg | |
| 5,431,627 A | 7/1995 | Pastrone et al. | |
| 5,441,636 A | 8/1995 | Chevallet et al. | |
| 5,474,683 A | 12/1995 | Bryant et al. | |
| 5,578,070 A | 11/1996 | Utterberg | |
| 5,614,677 A | 3/1997 | Wamsiedler et al. | |
| 5,628,908 A | 5/1997 | Kamen et al. | |
| 5,643,205 A | 7/1997 | Utterberg | |
| 5,674,397 A * | 10/1997 | Pawlak et al. | 210/436 |
| 5,989,423 A | 11/1999 | Kamen | |
| 6,179,801 B1 | 1/2001 | Holmes et al. | |
| 6,196,987 B1 | 3/2001 | Holmes et al. | |
| 6,200,287 B1 | 3/2001 | Keller et al. | |
| 6,231,537 B1 | 5/2001 | Holmes et al. | |
| 6,234,989 B1 | 5/2001 | Brierton et al. | |
| 6,280,406 B1 | 8/2001 | Dolecek et al. | |
| 6,337,049 B1 | 1/2002 | Tamari | |
| 6,361,518 B1 | 3/2002 | Brierton et al. | |
| 6,383,158 B1 | 5/2002 | Utterberg | |
| 6,409,696 B1 | 6/2002 | Toavs et al. | |
| 6,471,855 B1 | 10/2002 | Odak et al. | |
| 6,497,674 B1 | 12/2002 | Steele et al. | |
| 6,514,225 B1 | 2/2003 | Utterberg et al. | |
| 6,542,761 B1 | 4/2003 | Jahn et al. | |
| 6,645,166 B2 | 11/2003 | Scheunert et al. | |
| 6,695,803 B1 | 2/2004 | Robinson et al. | |
| 6,725,726 B1 | 4/2004 | Adolfs et al. | |
| 6,730,055 B2 | 5/2004 | Bainbridge et al. | |
| 6,755,801 B2 | 6/2004 | Utterberg et al. | |
| 6,764,761 B2 | 7/2004 | Eu et al. | |
| 6,790,195 B2 | 9/2004 | Steele et al. | |
| 6,852,090 B2 | 2/2005 | Burbank et al. | |
| 7,021,148 B2 | 4/2006 | Kuhn et al. | |
| 7,115,107 B2 | 10/2006 | Delnevo et al. | |
| 7,147,613 B2 | 12/2006 | Burbank et al. | |
| 7,195,607 B2 | 3/2007 | Westberg et al. | |
| 7,517,387 B2 | 4/2009 | Chevallet et al. | |
| 2002/0062109 A1 | 5/2002 | Lauer | |
| 2002/0072718 A1 | 6/2002 | Brugger et al. | |
| 2003/0042181 A1 | 3/2003 | Metzner | |
| 2003/0100882 A1 | 5/2003 | Beden et al. | |
| 2003/0220607 A1 | 11/2003 | Busby et al. | |
| 2004/0019313 A1 | 1/2004 | Childers | |
| 2004/0084647 A1 | 5/2004 | Beden et al. | |
| 2005/0054968 A1 | 3/2005 | Giannella | |
| 2005/0230292 A1 | 10/2005 | Beden et al. | |
| 2007/0193940 A1 | 8/2007 | Duchamp et al. | |
| 2007/0269340 A1 | 11/2007 | Dannenmaier et al. | |
| 2009/0088675 A1 | 4/2009 | Kelly et al. | |
| 2009/0192447 A1 | 7/2009 | Andersen et al. | |
| 2010/0145249 A1 * | 6/2010 | Myrick et al. | 604/4.01 |

FOREIGN PATENT DOCUMENTS

| | | |
|---|---|---|
| DE | 100 46 651 | 4/2002 |
| DE | 100 53 441 | 5/2002 |
| DE | 101 57 924 | 5/2002 |
| DE | 101 43 137 | 4/2003 |
| EP | 0728509 | 8/1996 |
| EP | 1529545 | 5/2005 |
| WO | WO 84/02473 | 7/1984 |
| WO | WO8705225 A1 | 9/1987 |
| WO | WO 98/22165 | 5/1998 |
| WO | WO 00/23140 | 4/2000 |
| WO | WO 00/33898 | 6/2000 |
| WO | WO 01/17605 | 3/2001 |
| WO | WO2008/125893 | 10/2008 |

OTHER PUBLICATIONS

Gambro®, Prisma® HF 1000, "For Increased Filtration Capacity", © Aug. 2001, Gambro Renal Products, Inc., Lakewood, CO, 2 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Gambro®, "Prismaflex™ anticipating critical care needs and taking our innovative response . . . to new heights," ©2004, Gambro Inc., Lakewood, CO, 8 pp.

Manns, Markus et al., "The acu-men: A new device for continuous renal replacement therapy in acute renal failure," Kidney International, vol. 54, pp. 268-274, 1998.

International Search Report and Written Opinion; PCT/US2011/024697; mailed Jul. 6, 2011.

Notification concerning Transmittal of International Preliminary Report on Patentability for corresponding PCT Application No. PCT/US2011/024697, mailed Sep. 20, 2012, 8 pages.

* cited by examiner

DIALYSIS SYSTEM VENTING DEVICES AND RELATED SYSTEMS AND METHODS

TECHNICAL FIELD

This invention relates to dialysis system venting devices and related systems and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semipermeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with sterile aqueous solution, referred to as PD solution or dialysate. The membranous lining of the patient's peritoneum acts as a natural semipermeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect of the invention, a dialysis system includes a fluid inlet line, a venting device including a housing defining a fluid chamber in fluid communication with the fluid inlet line and a valve member disposed above the fluid chamber between a lower seat defining an aperture and an upper seat defining an aperture, a fluid outlet line in fluid communication with the venting device such that fluid exiting the venting device flows through the fluid outlet line, and a pump that is operable to draw fluid into the fluid chamber via the fluid inlet line and to force fluid out of the fluid chamber via the fluid outlet line.

In another aspect of the invention, a venting device includes a housing defining a chamber, a liquid inlet port, and a liquid outlet port. The venting device further includes a reciprocatable member configured to change a pressure within the chamber as the reciprocatable member reciprocates and a buoyant valve member disposed above the chamber between a lower seat defining an aperture and an upper seat defining an aperture. The buoyant member is configured to seal the aperture of the lower seat when the reciprocatable member is moved in a first direction and to seal the aperture of the upper seat when the reciprocatable member is moved in a second direction.

In a further aspect of the invention, a venting method includes drawing dialysis fluid into a fluid chamber of a venting device by applying vacuum pressure to the fluid chamber, wherein gas is released from the dialysis fluid within the fluid chamber. The method further includes forcing the gas out of the fluid chamber by applying positive pressure to the fluid chamber for a first period of time, and then forcing the dialysis fluid out of the fluid chamber by continuing to apply positive pressure for a second period of time.

Implementations can include one or more of the following features.

In some implementations, the dialysis system further includes a sorbent device in fluid communication with the fluid inlet line such that fluid flows through the fluid inlet line after the fluid exits the sorbent device.

In certain implementations, the dialysis system further includes a sensor positioned along the fluid outlet line, the sensor configured to measure one or more parameters of fluid flowing through the fluid outlet line.

In some implementations, the venting device is positioned between the sorbent device and the sensor.

In certain implementations, the sensor is a conductivity sensor configured to measure a conductivity of fluid flowing through the fluid outlet line.

In some implementations, the dialysis system further includes a dialyzer in fluid communication with the fluid outlet line such that fluid flows through the dialyzer after exiting the venting device.

In certain implementations, the dialysis system further includes an inlet check valve positioned along the fluid inlet line and an outlet check valve positioned along the fluid outlet line.

In some implementations, the inlet check valve has a greater flow resistance than the valve member such that fluid more easily passes through the apertures in the upper and lower seats then through the inlet check valve when negative pressure is applied to the fluid chamber.

In certain implementations, the outlet check valve has a greater flow resistance than the valve member such that fluid more easily passes through the apertures in the upper and lower seats then through the outlet check valve when positive pressure is applied to the fluid chamber.

In some implementations, the venting device is configured so that the fluid chamber is in communication with atmospheric air when the valve member is not seated against the lower seat or the upper seat such that gases can be vented from the fluid chamber to the atmospheric air via the apertures.

In certain implementations, the housing of the venting device includes a membrane that can be deformed to alter the volume of the fluid chamber.

In some implementations, the pump includes a piston configured to deform the membrane.

In certain implementations, the dialysis system includes a dialysate component carrier having a base, and the venting device is attached to the base of the dialysate component carrier.

In some implementations, the dialysis system further includes a second venting device, wherein the venting devices are arranged such that fluid can be drawn into one of the venting devices as fluid is being expelled from the other venting device.

In certain implementations, the dialysis system further includes a fluid reservoir positioned between the sorbent device and the venting device, the fluid reservoir being in fluid communication with both the sorbent device and the venting device.

In some implementations, the fluid reservoir includes a collapsible container.

In certain implementations, the fluid inlet line is connected to a port formed in a top region of the flexible container.

In some implementations, the fluid reservoir is sized to contain about 50 milliliters to about 100 milliliters of fluid.

In certain implementations, the valve member is a ball.

In some implementations, the ball is buoyant.

In certain implementations, the ball is hollow.

In some implementations, the pump is a piston pump.

In certain implementations, the dialysis system is a hemodialysis system.

In some implementations, the dialysis system is a peritoneal dialysis system.

In certain implementations, the dialysis system is configured so that dialysate flows through the venting device during use.

In some implementations, the dialysis system is configured so that blood flows through the venting device during use.

In certain implementations, a valve member is positioned above the fluid chamber between a lower seat defining an aperture and an upper seat defining an aperture.

In some implementations, drawing dialysis fluid into the fluid chamber involves drawing the valve member against the lower seat to seal the aperture defined by the lower seat.

In certain implementations, prior to forcing the dialysis fluid out of the fluid chamber, the valve member is forced against the upper seat to seal the aperture defined in the upper seat.

In some implementations, the vacuum pressure is applied to the fluid chamber by moving a reciprocatable member connected to the venting device in a first direction, and the positive pressure is applied to the fluid chamber by moving the reciprocatable member connected to the venting device in a second direction opposite the first direction.

In certain implementations, the dialysis fluid is drawn into fluid chamber from a dialysis fluid reservoir, the dialysis fluid reservoir being sized to contain a larger volume of fluid than the fluid chamber.

Implementations can include one or more of the following advantages.

In some implementations, the systems and methods permit gases to be removed from dialysate before the conductivity of the dialysate is measured during dialysis treatment. In certain cases, the conductivity readings are then used to determine the amount of a substance, such as sodium, within the dialysate, and that information is used to determine a desired amount of an additive (e.g., sodium chloride solution or dilution water) to be added to the dialysate in order to achieve a desired concentration of the substance within the dialysate. Removing gas from the dialysate prior to taking the conductivity measurements can improve the ability of the system to determine the amount of the substance within the dialysate and can thus improve the ability of the system to determine the correct amount of additive to be added to the dialysate. As a result, the actual concentration of the substance within the dialysate can be maintained within a desired range throughout treatment.

Removal of gas from dialysis fluid (e.g., dialysate or blood) can also help to improve patient comfort during and after dialysis treatment. For example, removing gas from the dialysate and/or the blood of a patient undergoing hemodialysis treatment advantageously helps to ensure that gas bubbles do not enter the patient via the treated blood that is returned to the patient. In the case of peritoneal dialysis, removal of gas from the dialysate prior to introducing the dialysate into the abdominal cavity of the patient helps to reduce the build up of gases within the patient's abdominal cavity during treatment, and thus increases the comfort of the patient.

In certain implementations, the venting device includes a pump (e.g., a piston pump) that can be operated in a manner to alter the pressure within a fluid chamber of the venting device. Changing the pressure within the fluid chamber can help to ensure that the valve assembly of the venting device remains in an operable condition throughout the treatment. For example, regulating the pressure within the fluid chamber relative to the atmospheric pressure can help to ensure that the valve member (e.g., the ball) of the valve assembly does not become attached to the upper or lower seats of the venting device for a prolonged period of time due to a pressure differential between the fluid chamber and the atmospheric pressure. Regulating the pressure within the fluid chamber can, for example, help to ensure that the valve member does not become attached to the upper seat of the venting device until a desired volume of air has been released from the fluid chamber via the aperture in the upper seat.

In some implementations, the venting device is connected to a fluid reservoir (e.g., a dialysate reservoir) that has a substantially larger volume than the fluid chamber of the venting device. In certain implementations, this arrangement allows the venting device to be entirely devoted to removing gas from the fluid reservoir. For example, the venting device can draw the fluid and gas into the venting device, vent the gas to atmosphere, and then return the substantially gas-free fluid back to the fluid reservoir. Because in such implementations the venting device is not responsible for pumping the fluid through the remainder of the fluid circuit (e.g., to other downstream components of the system), the rate at which the fluid is circulated through the fluid circuit is independent of the pumping rate of the venting device.

In certain implementations, the venting device is connected via a venting line or tube to a container (e.g., a bag) that is vented to atmosphere. The venting line can be used to transfer gases forced out of the venting device to the container. Because the container is vented to atmosphere, upon reaching the container, the gases are released to the atmosphere. In addition, any liquid (e.g., dialysate) that escapes from the venting device via the venting line will be collected in the container. This arrangement can help to prevent spillage of liquids that can create a mess and that, in certain cases, can require time consuming sanitary measures to be taken.

Other aspects, features, and advantages of the invention will be apparent from the description and drawings, and from the claims.

DETAILED DESCRIPTION

Figure 1:
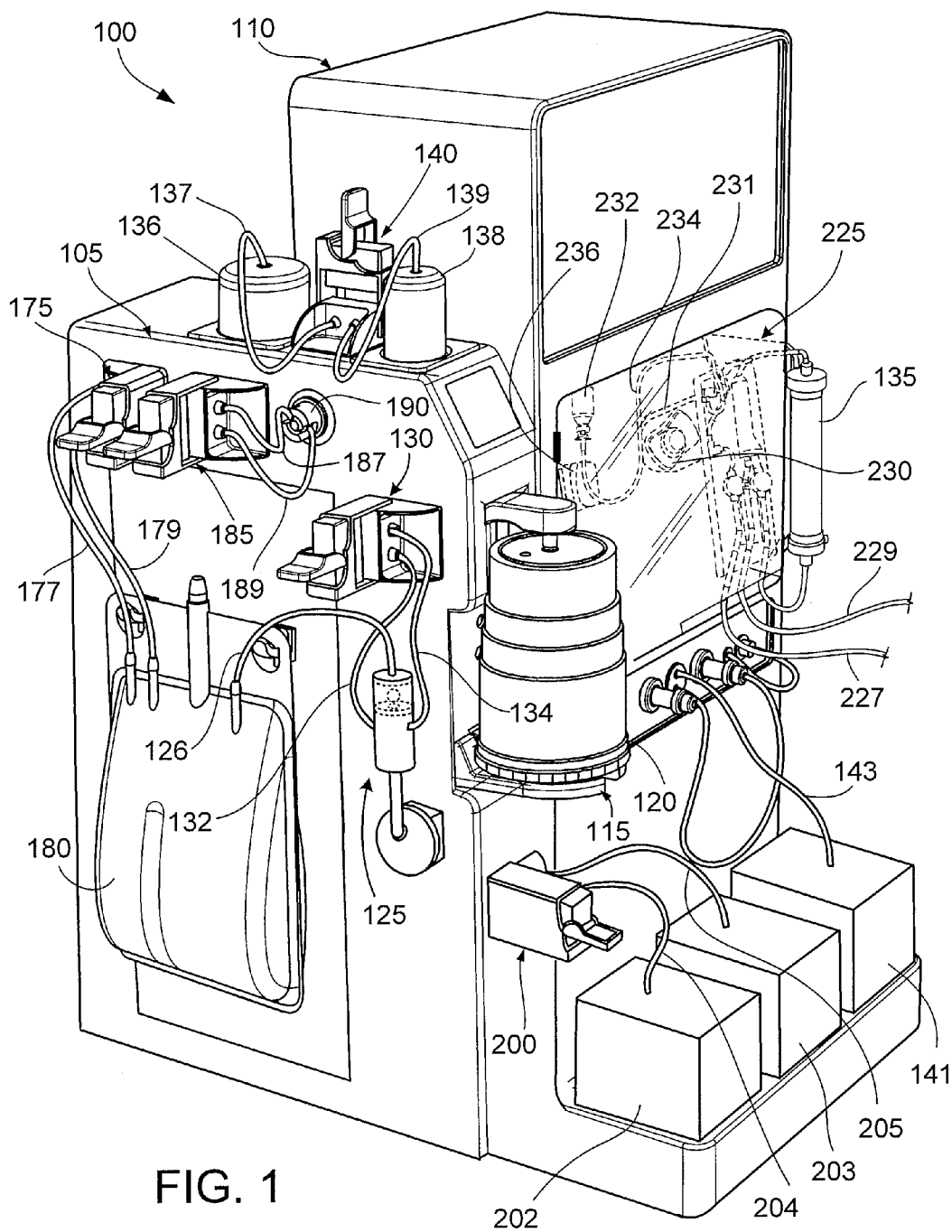
FIG. 1 is a perspective view of a hemodialysis system that includes a hemodialysis machine connected to a module with a sorbent device for recycling spent dialysate.

FIG. 1 shows a hemodialysis system 100 that includes a module 105 fluidly coupled to a hemodialysis machine 110. The module 105 includes, among other things, a sorbent device holder 115 that holds a sorbent device 120. The module also includes a venting device 125 that is connected to a manifold 130 of the module 105 via inlet and outlet lines 132, 134 and is connected to a vented bag 180 via a venting line 126. As will be described in greater detail below, the module 105 is used to recycle spent dialysate so that the spent dialysate can be reused for hemodialysis treatment. During use of the hemodialysis system 100, dialysate is pumped from the module 105 to the hemodialysis machine 110. The dialysate is then passed through a dialyzer 135' connected to the hemodialysis machine 110 at the same time that a dialysis patient's blood is passed through the dialyzer 135. As a result, toxins, such as urea, migrate across a permeable membrane (e.g., hollow fibers) of the dialyzer 135 from the patient's blood to the dialysate, producing spent dialysate (i.e., dialysate that contains toxins removed from the patient's blood). The spent dialysate is pumped to the module 105 where it passes through the sorbent device 120, which removes toxins from the spent dialysate. As a result of chemical reactions that occur within the sorbent device 120, the recycled dialysate exiting the sorbent device 120 typically contains gas, such as carbon dioxide. After exiting the sorbent device 120, the recycled dialysate travels into the module 105 and then is drawn into the venting device 125 via the inlet line 132, which is connected to the manifold 130 of the module 105. The recycled dialysate is then forced from the venting device 125 back into the module 105 via the outlet line 134, which is connected to the manifold 130 of the module 105. Gas that is present in the recycled dialysate is advantageously delivered to the bag 180 via the venting line 126 and vented to atmosphere due to the operation of the venting device 125, as will be described in greater detail below. The recycled dialysate is then cycled back through the dialysate circuit and reused to cleanse the dialysis patient's blood.

Certain desired substances (e.g., magnesium, calcium, potassium, and sodium) may be stripped from the dialysate as the dialysate passes through the sorbent device 120. Those stripped substances can be added to the dialysate exiting the sorbent device 120. As shown in FIG. 1, an infusate solution container 136 and a sodium chloride solution container 138 are connected to a manifold 140 of the module 105 via fluid lines 137 and 139, respectively. The infusate solution (e.g., a solution including magnesium, calcium, and potassium) and sodium chloride can be drawn into the dialysate flowing within the module 105 by activating associated valves and pumps within the module 105.

As shown in FIG. 1, a dilution water container 141 is connected to the dialysis machine 110 via a fluid line 143. In some cases, certain substances, such as sodium, may be added to, rather than stripped from, the dialysate as the dialysate passes through the sorbent device 120. As a result, the sodium concentration in the dialysate exiting the sorbent device 120 may exceed a maximum desired concentration. In such cases, dilution water can be added to dialysate that is exiting the hemodialysis machine 110 and flowing into the module 105 toward the sorbent device 120. The dilution water can be added to the dialysate exiting the hemodialysis machine 110 by activating a pump within the hemodialysis machine 110. Activating this pump draws the dilution water from the dilution water container 141 and fluid line 143 into the dialysate exiting the hemodialysis machine 110 such that the sodium concentration of the dialysate exiting the hemodialysis machine 110 (and eventually flowing through the module 105) is reduced, as will be described in greater detail below.

The sodium concentration of the dialysate passing through the dialyzer 135 affects (e.g., increases or decreases) the sodium concentration in the patient's blood. If the sodium concentration in the patient's blood falls outside a desired range, the patient may experience discomfort or illness. For this reason, a conductivity meter 145 (shown in FIG. 8) is positioned within the module 105 to measure the conductivity of dialysate after the dialysate exits the sorbent device 120. These conductivity readings are used during treatment to determine the amount of sodium chloride solution or dilution water to be added to the recycled dialysate exiting the sorbent device 120. In particular, because the sodium in the dialysate is the predominant contributor to the conductivity of the dialysate, the sodium concentration of the dialysate can be determined or approximated based on the conductivity readings. The amount of sodium chloride solution or dilution water to add to the dialysate in order to achieve a desired sodium concentration within the dialysate can then be determined.

Gas within the dialysate can affect the conductivity readings measured by the conductivity meter 145 and can thus cause the approximated sodium concentration of the dialysate to differ substantially from the actual sodium concentration of the dialysate. By using the venting device 125 to remove gas from the recycled dialysate before the recycled dialysate passes through the conductivity meter 145 in the module 105, the approximation of the sodium concentration based on the conductivity readings can more accurately reflect the actual sodium concentration in the dialysate. Thus, removing the gas from the dialysate helps to ensure that the sodium chloride solution or dilution water is added to the dialysate in a manner to maintain the sodium concentration of the dialysate and of the patient's blood within a desired range throughout treatment.

Figure 2:
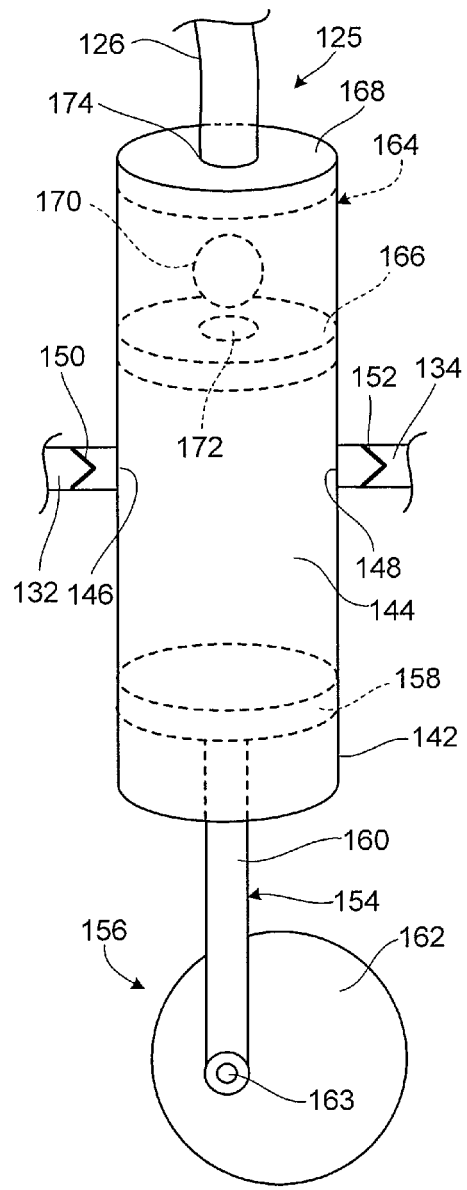
FIG. 2 is a perspective view of a venting device of the hemodialysis system of FIG. 1.
Figure 3:
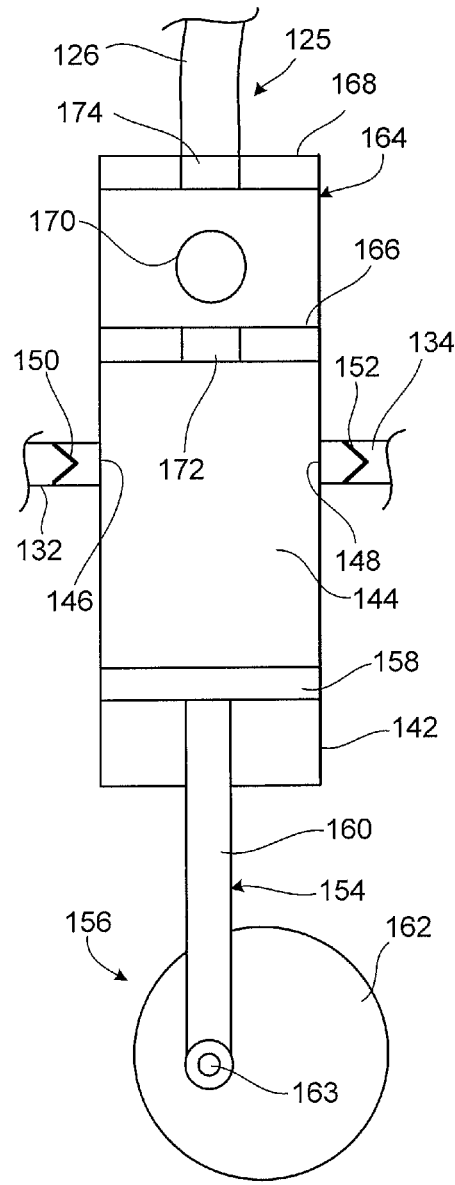
FIG. 3 is a schematic cross-sectional view of the venting device of FIG. 2.

FIG. 2 is an enlarged schematic view of the venting device 125, and FIG. 3 is a cross-sectional schematic view of the venting device 125. As shown in FIG. 3, the venting device 125 has a housing 142 that forms a fluid chamber 144, an inlet port 146, and an outlet port 148. The inlet line 132 is connected to the inlet port 146, and the outlet line 134 is connected to the outlet port 148. Inlet and outlet check valves 150 and 152 are positioned within the inlet and outlet ports 146 and 148, respectively. The inlet check valve 150 is configured so that, under normal operating conditions, dialysate can enter the fluid chamber 144 via the inlet port 146 but cannot exit the fluid chamber 144 via the inlet port 146. Similarly, the outlet check valve 152 is configured so that, under normal operating conditions, dialysate can exit the fluid chamber 144 via the outlet port 148 but cannot enter the fluid chamber 144 via the outlet port 148. Any of various different types of check valves can be used. Examples of suitable check valves include elastomeric duck-bill check valves, ball and spring check valves, electrically actuated check valves, flap check valves, diaphragm check valves, and swing gate check valves.

A piston 154 of a piston pump 156 extending from the module 105 is positioned in the fluid chamber 144 of the venting device 125 when the venting device 125 is assembled and connected to the module 105. The piston 154 includes a piston head 158 secured to a piston shaft 160. To assemble the venting device 125, the piston head 158 is inserted into the fluid chamber 144, and the piston shaft 160 is operatively connected to a rotatable disk 162 of the pump 156. The piston shaft 160 can, for example, be secured to the rotatable disk 162 by positioning a pin 163 within aligned holes extending through the piston shaft 160 and the rotatable disk 162 so that the both the piston shaft 160 and the rotatable disk 162 can be rotated relative to the pin 163 during use. The piston head 158 is formed of a resilient material that becomes deformed within the fluid chamber 144 to form a fluid-tight seal with the inner surface of the portion of the housing 142 forming the fluid chamber 144 during use. When the piston pump 156 is operated, the disk 162 rotates, causing the piston head 158 to reciprocate within the fluid chamber 144.

Still referring to FIG. 3, a ball valve assembly 164 is provided near the top of the fluid chamber 144. The ball valve assembly 164 includes a lower seat 166, an upper seat 168, and a buoyant ball 170 positioned between the lower and upper seats 166, 168. The lower and upper seats 166, 168 include apertures 172, 174, respectively, that are sized and shaped to receive a portion of the ball 170 without allowing the ball 170 to pass all the way through the apertures 172, 174. The lower and upper seats 166, 168 otherwise include no holes or passages. Thus, when the ball 170 is pressed or drawn against the lower seat 166 with sufficient force, a fluid-tight seal (e.g., a liquid-tight and gas-tight seal) is formed between the ball 170 and the portion of the lower seat 166 forming the aperture 172. In the same manner, when the ball 170 is pressed or drawn against the upper seat 168 with sufficient force, a fluid-tight seal (e.g., a liquid-tight and gas-tight seal) is formed between the ball 170 and the portion of the upper seat 168 forming the aperture 174.

The upper and lower seats 166, 168 can be fabricated separately from the housing 142 and then attached (e.g., thermally bonded or adhesively bonded) to the housing 142. Alternatively, injection molding techniques can be used to integrally mold the housing 142 and the upper and lower seats 166, 168.

The ball 170 can be a hollow member formed of one or more polymeric materials, such as polyethylene terephthalate (PETE), polyvinyl chloride (PVC), high density polyethylene (HDPE), low density polyethylene (LDPE), polypropylene, and/or polystyrene. Due to this construction, the ball 170 is able to float in dialysate. Alternatively, any of various other ball constructions that permit the ball 170 to float in dialysate can be used. For example, the hollow ball 170 can be constructed of any of various other materials, such as styrofoam, cork, rubber, wood, and/or certain metals, such as aluminum.

The venting line 126 is fluidly connected to the aperture 174 of the upper seat 168 in a manner that allows dialysate and/or gas exiting the venting device 125 via the aperture 174 to travel through the venting line 126 to the vented bag 180. Any of various techniques can be used to connect the venting line 126 to upper seat 168 in this manner. For example, the venting line 126 can be thermally bonded, adhesively bonded, and/or mechanically attached to the upper seat 168.

Figure 4:
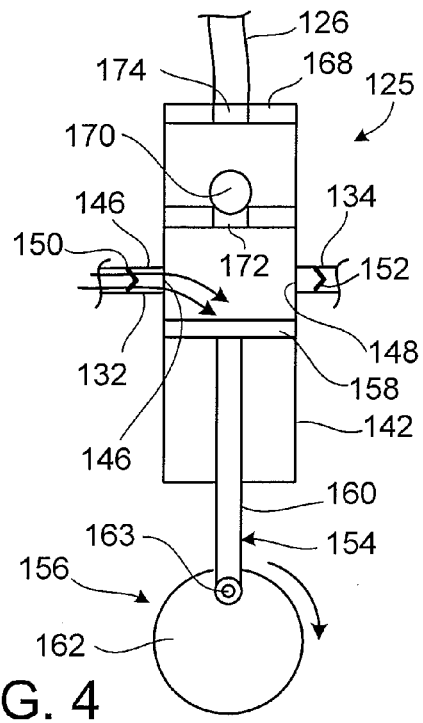
FIGS. 4-7 illustrate a method of venting gas from dialysate by drawing a mixture of dialysate and gas into a fluid chamber of the venting device and then separately expelling the gas and the dialysate from the fluid chamber of the venting device.

FIGS. 4-7 illustrate a method of using the venting device 125 to vent gas from the dialysate circuit. As shown in FIG. 4, when the piston head 158 is retracted within the fluid chamber 144 (i.e., moved away from the ball valve assembly 164), the ball 170 is drawn against the lower seat 166 forming a fluid-tight seal. The inlet check valve 150 has a resistance such that dialysate is not initially drawn into the fluid chamber 144 via the inlet line 132 when the piston 154 is retracted. However, once the ball 170 becomes seated on the lower seat 166 to form a fluid-tight seal, the retraction of the piston head 158 increases the vacuum within the fluid chamber 144 such that the vacuum pressure within the fluid chamber 144 becomes sufficient to overcome the resistance of the inlet check valve 150. In certain implementations, for example, the inlet check valve 150 is constructed to prevent fluid flow therethrough until the vacuum pressure within the fluid chamber 144 reaches about −0.1 psi to about −5 psi (e.g., about −2 psi). As the resistance of the inlet check valve 150 is overcome, dialysate is drawn into the fluid chamber 144 via the inlet line 132. As noted above, in some cases, the dialysate contains gas that is also drawn into the fluid chamber 144. The negative pressure within the fluid chamber 144 can help to draw the air out of the dialysate such that the air and dialysate are separated within the fluid chamber 144. As the dialysate and gas are drawn into the fluid chamber 144, the fluid-tight seal between the ball 170 and the lower seat 166 prevents air from entering the fluid chamber 144 via the ball valve assembly 164, and the outlet check valve 152 prevents recycled dialysate from entering the fluid chamber 144 via the outlet line 134.

Figure 5:
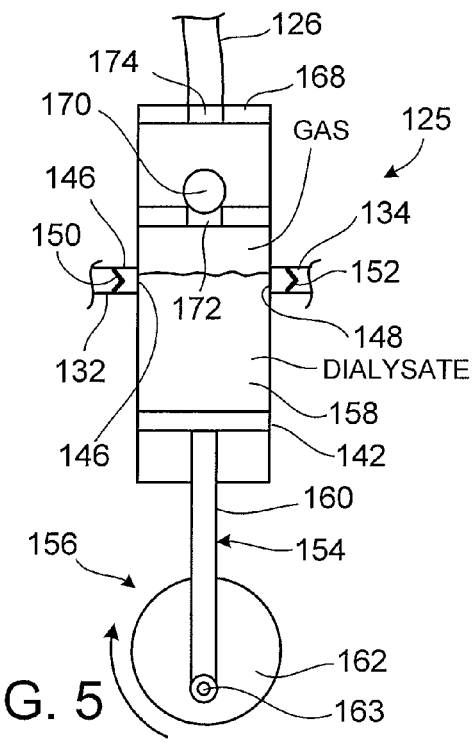

As shown in FIG. 5, dialysate is drawn into the fluid chamber 144 until the piston 154 reaches the bottom of its reciprocating piston stroke. The reciprocating stroke of the piston 154 can be selected to draw a desired volume of fluid (e.g., dialysate and gas) into the fluid chamber 144 when the piston 154 is retracted. In certain implementations, about 50 milliliters to about 100 milliliters of fluid is drawn into the fluid chamber 144 when the piston 154 is retracted. As the dialysate and gas mixture is drawn into the fluid chamber 144, the gas released from the dialysate collects in the top region of the fluid chamber 144.

Figure 6:
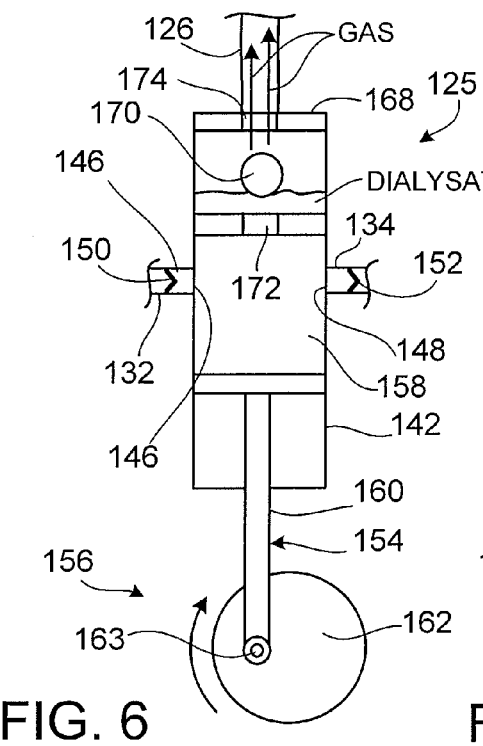

As shown in FIG. 6, after reaching the bottom of the piston stroke, the piston 154 is forced upward through the fluid chamber 144 by continuing to rotate the disk 162 of the piston pump 156. This upward movement of the piston 154 creates a positive pressure within the fluid chamber 144. The outlet check valve 152 is constructed with a resistance such that the dialysate is not allowed to pass through the outlet check valve 152 until the pressure within the fluid chamber 144 reaches a minimum pressure value. In certain implementations, for example, the outlet check valve 152 is constructed to prevent fluid flow therethrough until the pressure within the fluid chamber 144 reaches about 0.1 psi to about 5 psi (e.g., about 2 psi). Thus, during the initial phase of the upstroke of the piston 154, the path of least flow resistance for fluid to exit the fluid chamber 144 is via the apertures 172, 174 of the ball valve assembly 164. As a result, gas within the fluid chamber 144, which tends to collect near the top of the fluid chamber 144, is forced through the aperture 172 of the lower seat 166, around the ball 170, and out the aperture 174 of the upper seat 168 to the bag 180 (shown in FIG. 1) via the venting line 126 as the piston 154 is driven in the upward direction. The bag 180 is vented to atmosphere such that any gases driven out of the fluid chamber 144 to the bag 180 are ultimately released to the atmosphere. The bag 180 can, for example, include an opening or a porous membrane (e.g., hydrophobic membrane) that permits gases to pass therethrough.

As the piston 154 continues to move upward, the liquid level (i.e., the dialysate level) within the fluid chamber 144 rises and eventually reaches the ball 170. Due to the buoyancy of the ball 170, the upward moving dialysate causes the ball 170 to move upward toward the upper seat 168. Typically, very little or none of the dialysate will escape through the aperture 174 of the upper seat 168 during the upstroke of the piston 154. However, in the event that some of the dialysate happens to escape through the aperture 174, that dialysate will travel through the venting line 126 and be collected in the bag 180. As a result, that dialysate, along with the remainder of the dialysate in the bag 180, can be recirculated through the system.

Figure 7:
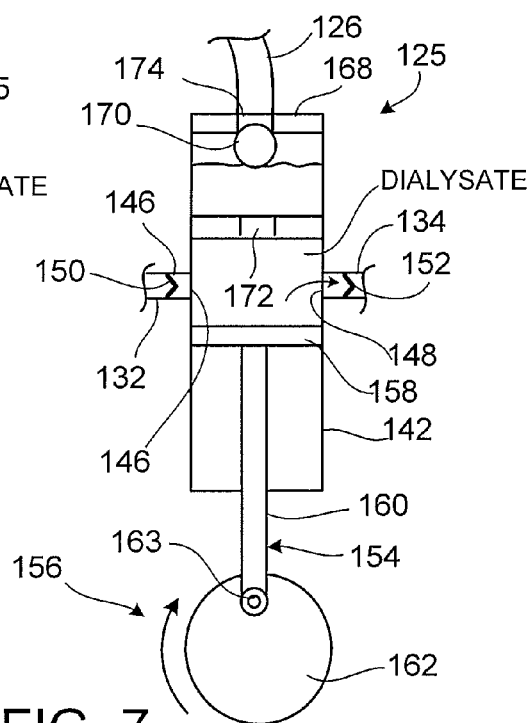

After forcing most of the gas (e.g., substantially all of the gas) through the aperture 174 and the venting line 126, the rising dialysate causes the ball 170 to contact the upper seat 168, as shown in FIG. 7. Continuing upward movement of the piston 154 causes the ball 170 to be pressed against the upper seat 168 with sufficient pressure to create a fluid-tight seal between the ball 170 and the upper seat 168. Subsequent upward movement of the piston 154 increases the pressure within the fluid chamber 144 until the pressure is sufficient to overcome the resistance of the outlet check valve 152. Upon reaching a pressure sufficient to overcome the resistance of the outlet check valve 152, the dialysate is forced out of the fluid chamber 144 via the outlet line 134.

After the piston 154 reaches the top of the piston stroke and has expelled the dialysate from the fluid chamber 144, the continued rotation of the disk 162 of the piston pump 156 retracts the piston head 158 through the fluid chamber 144 and dialysate is again drawn into the fluid chamber 144. With typical dialysate flow rates of about 500 ml/min, the piston pump 156 is operated at a speed of about 5 strokes per minute.

The process described above of venting gases from the fluid chamber 144, and then expelling the dialysate from the fluid chamber 144 is then repeated. This process can be continuously repeated throughout the dialysis treatment.

Periodically increasing and decreasing the pressure within the fluid chamber 144 by reciprocating the piston 154 helps to ensure that the ball 170 does not get stuck (e.g., due to a pressure differential between the fluid chamber 144 and the atmosphere) to the lower seat 166 or the upper seat 168 during treatment. This helps to ensure that gas can be predictably vented from the fluid chamber 144 throughout dialysis treatment.

Referring again to FIG. 1, in addition to the manifolds 130 and 140, the module 105 includes a manifold 175 to which fluid lines 177, 179 extending from the bag 180 are connected and a manifold 185 to which fluid lines 187, 189 extending from an ammonium ($NH_4$) sensor 190 are connected. The module 105 further includes a manifold 200 by which a fresh dialysate container 202 and a drain container 204 are connected to the module 105 via a fluid line 204 and a drain line 205, respectively. Each of manifolds 130, 140, 175, 185, and 200 can, for example, include projections on which fluid lines can be positioned to connect the various components described above to their respective manifold. Any of various other suitable connection mechanisms can alternatively or additionally be used to connect the fluid lines to the manifolds.

The manifold 175 allows dialysate to be transferred from the module 105 to the bag 180 and vice versa. In particular, using pumps and valves within the module 105, dialysate can be pumped into and suctioned out of the bag 180 via the fluid lines 177, 179 connected to the manifold 175. The manifold 185 permits dialysate to be transferred from the module 105 to the ammonium sensor 190 and vice versa. By activating pumps and valves within the module 105 in a desired manner, the dialysate can be pumped from the module 105 to the ammonium sensor 190 and can be drawn back to the module 105 from the ammonium sensor 190. By activating pumps and valves within the module, fluid can be drawn into the module 105 from the fresh dialysate container 202 via the fluid line 204, and fluid can be pumped from the module 105 to the drain container 203 via the drain line 205. With the sorbent device 120 positioned in the cartridge holder 115, as shown in FIG. 1, fluid circulating within the module 105 is allowed to pass through the sorbent device 120 to recycle the dialysate.

Still referring to FIG. 1, a blood component set 225 is secured to a front face of the hemodialysis machine 110. The blood component set 225 includes arterial and venous patient lines 227, 229 that are connected to a patient during treatment. The arterial patient line 227 is connected to an inlet port of the dialyzer 135 via a series of blood lines, and the venous patient line 229 is connected to an outlet port of the dialyzer 135 via a series of blood lines. A blood pump line 231 positioned between the arterial patient line 227 and the dialyzer 135 is operably connected to a peristaltic blood pump 230 extending from the front face of the hemodialysis machine 110. The peristaltic blood pump 230 can be operated to pump blood through the various blood lines and components of the blood component set 225. In particular, operation of the blood pump 230 draws blood from the patient through the arterial patient line 227. The blood continues through a series of blood lines and blood components (e.g., sensors) to the dialyzer 135. The blood exits the dialyzer 135 and passes through another series of blood lines and components (e.g., sensors) and then is returned to the patient via the venous patient line 229.

As the blood is pumped through the various blood lines and components of the blood component set 225, it may be desirable to inject certain substances, such as drugs and/or saline into the blood lines. As shown in FIG. 1, a drug vial (e.g., a heparin vial) 232 is connected to one of the blood lines via a drug delivery line 234. The drug delivery line 234 is threaded through a peristaltic drug pump 236, which can be used to deliver the drug from the vial 232 to the blood circuit during treatment. A saline bag 238 is also connected to a blood line of the blood component set 225 via a priming line 240. This arrangement allows saline to be delivered through the blood circuit formed by the blood lines and components of the blood component set when desired.

Figure 8:
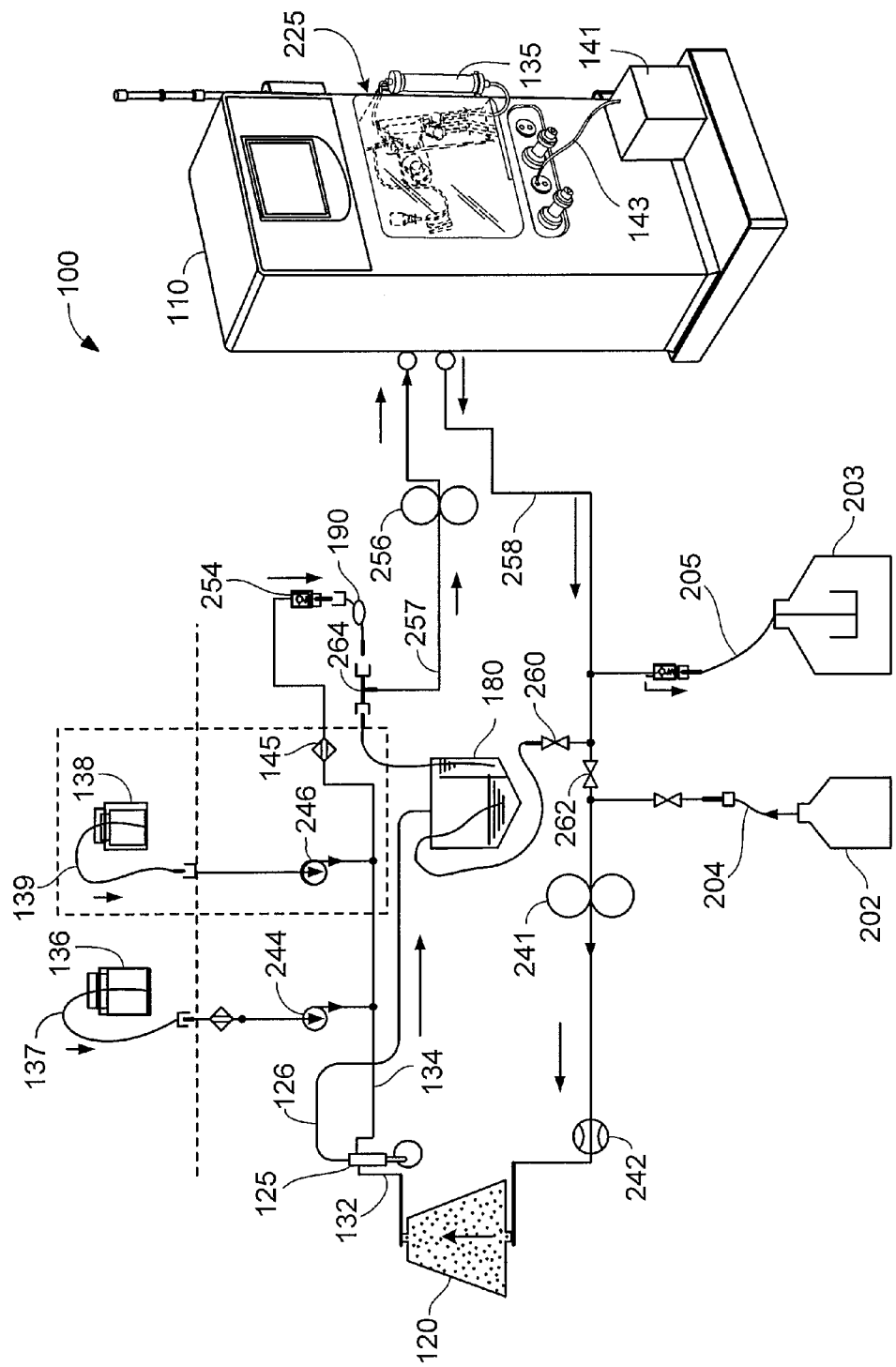
FIG. 8 is a schematic view of the various components of the module of FIG. 1 connected the hemodialysis machine of FIG. 1, which is illustrated in a perspective view.

FIG. 8 schematically illustrates the various components of the module 105 connected to the hemodialysis machine 110. Referring to FIG. 8, a method of performing hemodialysis will now be described. Prior to beginning the dialysis treatment, fresh dialysate is drawn into the module 105 from the fresh dialysate container 202 by selectively activating a pump 241 and various valves of the module 105. The fresh dialysate is then circulated through the module 105 by the pump 241. Prior to reaching the sorbent device 120, the dialysate passes through a flow meter 242 that is configured to measure the flow rate of the dialysate passing therethrough. A signal representing the flow rate of the dialysate can be transmitted from the flow meter 242 to a control unit (e.g., a microprocessor). The control unit can use the detected flow rate of the dialysate to control metering of the infusate solution into the dialysate.

As the dialysate passes through the sorbent device 120, certain substances, such as calcium, magnesium, potassium, and sodium may be stripped from the dialysate. As discussed above, the sorbent device 120 is also adapted to remove toxins, such as urea, from fluid flowing therethrough, but the fresh dialysate from the fresh dialysate container 202 would generally not contain any such toxins. Upon exiting the top of the sorbent device 120, the dialysate is passed through the fluid inlet line 132 to the venting device 125. As discussed above with respect to FIGS. 4-7, the dialysate and any gas that is contained in the dialysate is drawn into the fluid chamber 144 of the venting device 125 by operation of the piston pump 154. The gas and dialysate are then separately expelled from the fluid chamber 144 via the venting line 126 and fluid outlet line 134, respectively, by continued operation of the piston pump 154.

The infusate solution, which includes magnesium, calcium, and potassium, is then pumped into the fluid outlet line 134 from the infusate solution container 136 by activating a pump 244. As discussed above, the infusate solution can be added to the dialysate to restore concentrations of magnesium, calcium, and potassium to desired levels. Maintaining the concentration of these substances within the dialysis solution, such as calcium, magnesium, potassium, and sodium, can help to prevent the patient from experiencing discomfort during and after the treatment.

After introducing the infusate solution into the dialysate, the mixture of the dialysate and infusate solution continues to flow through the fluid outlet line 134 and passes through the conductivity meter 145. The conductivity meter 145 can estimate, based on the conductivity of the dialysate passing therethrough, the concentration of sodium within the dialysate. A pump 246 can then be activated in a manner to introduce sodium chloride solution into the fluid outlet line 134 from the sodium chloride solution container 138 if the conductivity reading indicates that the sodium level in the dialysate is lower than desired. The pump 246 can be operated in a manner to meter a desired volume of sodium chloride solution into the dialysate at a desired rate.

Similarly, a pump internal to the hemodialysis machine 110 can be activated to inject dilution water (e.g., tap water) from the dilution water container 141 into the dialysate exiting the hemodialysis machine 110 and entering the module 105 if the conductivity reading indicates that the sodium level in the dialysate is higher than desired. This dilution water pump can be operated in a manner to meter a desired volume of the dilution water into the dialysate at a desired flow rate.

A microprocessor is connected to the flow meter 242, the conductivity meter 145, and the pumps 156, 241, 244, 246, and 256. The microprocessor is also connected to the dilution water pump inside the hemodialysis machine 110. The measured flow rate of the dialysate is transmitted in the form of a signal from the flow meter 242 to the microprocessor. The microprocessor adjusts operation of the pumps 241 and 256 based on the measured flow rate at the flow meter 242 to ensure that a prescribed dialysate flow rate is achieved. The microprocessor also controls the pump 244 as a function of the flow rate of the dialysate measured by the flow meter 242. This arrangement helps to ensure that a desired amount of the infusate is added to the dialysate, and thus helps to ensure a desired proportion of the infusate to the dialysate.

In response to receiving the signals from the conductivity meter 145, the microprocessor sends signals to the pumps 244 and 246 to cause some of the sodium chloride solution, if desired, to be introduced into the fluid outlet line 134. Similarly, in response to receiving these signals from the conductivity meter 145, the microprocessor can cause the dilution water pump in the hemodialysis machine 110 to pump dilution water, if desired, into the dialysate exiting the hemodialysis machine 110 and entering the module 105. Removing gas from the dialysate solution with the venting device 125, as discussed above, helps to improve the accuracy with which the actual sodium concentration of the dialysate can be approximated based on the conductivity readings of the conductivity meter 145. As a result, the amount of sodium chloride and/or dilution water delivered to the dialysate can better achieve a desired sodium concentration within the dialysate (e.g., a sodium concentration that closely matches the sodium concentration prescribed by the dialysis patient's physician).

After passing through the conductivity meter 145, the dialysate passes through a check valve 254 and into the ammonium sensor 190, which detects ammonium levels within the dialysate.

After filling the bag 180 to a desired level with dialysate having a desired concentration of calcium, magnesium, potassium, and sodium, a pump 256 is activated to draw the dialysate from the bag 180 into the hemodialysis machine 110 via fluid line 257. The dialysate is circulated through the hemodialysis machine 110 and passes through the dialyzer 135 connected to the hemodialysis machine 110. At the same time, a patient's blood is circulated through the blood component set 225, including the dialyzer 135, connected to the hemodialysis machine 110. As a result, toxins, such as urea, are transferred across a permeable membrane (e.g., permeable microtubes) of the dialyzer 135 from the patient's blood to the dialysate. The spent dialysate exiting the dialyzer 135 is then routed back to the module 105.

The spent dialysate passes through a fluid line 258 in the module 105. Depending on the desired volume of dialysate to be cycled back to the dialysis machine, some of the spent dialysate can be routed to a spent dialysate chamber of the bag 180 via open valve 260 while the remainder of spent dialysate is routed toward the sorbent device via open valve 262. As a result of the dialysis, for example, fluid from the patient may be added to the dialysate as the dialysate passes through the dialyzer 135. Thus, routing some of the spent dialysate to the bag 180 can help to ensure that a substantially constant volume of dialysate is circulated through the module 105 and the hemodialysis machine 110 throughout treatment. The pump 241 along the fluid line 258 forces the volume of the spent dialysate that is not routed to the bag 180 into the sorbent device 120 via the cartridge holder 115. As the spent dialysate passes through the sorbent device 120, urea is removed from the spent dialysate. Calcium, magnesium, and potassium are also stripped from the spent dialysate by the sorbent device 120. The recycled dialysate, upon exiting the sorbent device 120, passes through the venting device 125 where gases that may be produced as a result of chemical reactions within the sorbent device 120 are removed from the recycled dialysate.

In the manner discussed above, after the recycled dialysate exits the sorbent device 120, the infusate solution is introduced into the recycled dialysate and, based on the conductivity reading at the conductivity meter 145, sodium chloride may be added to the recycled dialysate. Similarly, dilution water can be added to the spent dialysate exiting the hemodialysis machine 110 and entering the module 105 based on the reading at the conductivity meter 145. In the initial stages of treatment, sodium levels in the recycled dialysate tend to be lower than desired due to the tendency of the sorbent device 120 to strip sodium from the dialysate passing therethrough. Consequently, in the early stages of the treatment, sodium chloride will typically be injected into the fluid outlet line 134 to increase the concentration of sodium in the recycled dialysate. In later stages of the treatment, however, the sorbent device 120 may contain high levels of sodium and thus release sodium into the spent dialysate as the spent dialysate passes through the sorbent device 120. This can lead to higher than desired levels of sodium in the recycled dialysate passing through the fluid outlet line 134. In such cases, dilution water is injected into the spent dialysate exiting the hemodialysis machine 110 and entering the module 105 to lower the sodium concentration of the spent dialysate. This spent dialysate then travels through the module 105 to the sorbent device 120 where the dilution water and spent dialysate are filtered. Injecting the dilution water into the spent dialysate before the spent dialysate passes through the sorbent device 120 to be filtered allows the use of tap water as the dilution water because the tap water will be filtered and purified as it passes through the sorbent device 120. This arrangement permits the hemodialysis system 100 to be operated with a readily available supply of dilution water and without the need for storing large volumes of dilution water on site. As discussed above, removing gas from the recycled dialysate as the recycled dialysate passes through the venting device 125 helps to improve the accuracy of the readings of the conductivity meter 145 and thus helps to ensure that a desired amount of sodium chloride solution or dilution water is added to the recycled dialysate.

After flowing past the conductivity meter 145, the recycled dialysate passes through the check valve 254 and into the ammonium sensor 190. After exiting the ammonium sensor 190, some of the recycled dialysate is routed to the bag 180 and some of the recycled dialysate is routed to the hemodialysis machine 110. In particular, in order to ensure that an equal amount of fluid enters and exits the hemodialysis machine 110, a T-valve 264 is adapted to route a portion of the dialysate to the hemodialysis machine 110 via the fluid line 257 and to route excess dialysate to the fresh dialysate chamber of the bag 180. Because the flow rate of the dialysate at the T-valve 264 is generally greater than the rate at which the dialysate is being pulled into the hemodialysis machine 110, there will typically be excess dialysate passing through the T-valve 264 and that excess dialysate will be routed to the bag 180 where it is collected for later use.

The dialysate that is delivered to the hemodialysis machine 110 again passes through the dialyzer where toxins are transferred from the patient's blood to the dialysate. The spent dialysate is then routed back to the module and the process is repeated until a desired amount of toxins has been removed from the patient's blood.

After completing the patient's treatment, the dialysate can be removed from the bag 180. For example, the pumps and valves of the module 105 can be operated in a manner to pump the dialysate from the bag 180 into the drain container 203 or into a plumbing drain. Emptying the bag 180 can allow the user to more easily handle the bag 180 after treatment due to the decreased weight.

After draining the bag 180 to a desired level, the external components (e.g., the sorbent device 120, the venting device 125, the infusate container 136, the sodium chloride container 138, the bag 180, the dialysate container 202, the drain container 203, and their associated fluid lines), which are constructed as disposable, single use components, are disconnected from the module 105 and discarded.

While certain implementations have been described, other implementations are possible.

While the ball 170 of the venting device 125 has been described as being hollow, in certain implementations, the ball 170 can be a substantially solid member. In certain implementations, for example, the ball 170 is formed of cork or includes a cork core surrounded by a polymeric coating. Any of various other constructions that permit the ball 170 to float in dialysate can alternatively be used.

While the venting device 125 has been described as including a ball valve assembly 164 to facilitate the release of gas from the fluid chamber 144 of the venting device 125, any of various other types of valve assemblies can alternatively be used. In some implementations, for example, the valve assembly includes a buoyant rod that is tapered at both ends (e.g., a dual cone shaped rod). Like the ball 170, the rod can be used in combination with upper and lower seats having apertures sized to receive the tapered end regions of the rod without allowing the rod to pass entirely through the apertures. As a result, the rod can create fluid-tight seals with the upper and lower seats. During use, the tapered ends of the rod are positioned within the apertures of the upper and lower seats. As a result, when the dialysate level rises within the fluid chamber of the venting device to a certain level, the rod moves upward and into sealing engagement with the upper seat, and when the dialysate level drops below a certain level, the rod drops into sealing engagement with the lower seat. Valve members having any of various other shapes capable of creating a fluid-tight seal with the upper and lower seats can alternatively be used in the valve assembly of the venting device. In some implementations, for example, a disk-shaped or puck-shaped valve member is used.

In certain implementations, the surfaces of the upper and lower seats 166 and 168 that form the apertures 172 and 174 are tapered to help ensure proper engagement between the valve member and the upper and lower seats 166 and 168.

While the piston head 158 of the piston 154 has been described as being formed of a resilient material, any of various other arrangements that provide a fluid-tight seal between the piston head 158 and the portion of the housing 142 forming the fluid chamber 144 can be used. In some implementations, for example, the piston head is a relatively rigid member with a resilient o-ring positioned around its circumference to create a fluid-tight seal with the inner surface of the portion of the housing 142 forming the fluid chamber 144.

While the hemodialysis system 100 has been described as including a piston pump that cooperates with the venting device 125 to draw dialysate into the fluid chamber 144 of the venting device 125 and to force gas and dialysate out of the fluid chamber 144 of the venting device 125, other types of pumps can be used. In certain implementations, for example, a syringe pump is connected to the venting device 125 in a manner to draw dialysate into the fluid chamber 144 of the venting device 125 and then expel gases and dialysate from the fluid chamber 144.

While the hemodialysis system 100 has been described as including a single venting device, multiple venting devices can alternatively be used. In certain implementations, for example, two venting devices are positioned in parallel along the dialysate circuit. The fluid inlet line 132 and the fluid outlet line 134 can, for example, each be divided into a first branch that connects to one of the venting devices and a second branch that connects to the other venting device. This configuration allows dialysate to be expelled from one of the venting devices while dialysate is being drawn into the other venting device and vice versa. As a result, a substantially continuous flow of dialysate through the dialysate circuit can be maintained throughout treatment.

Figure 9:
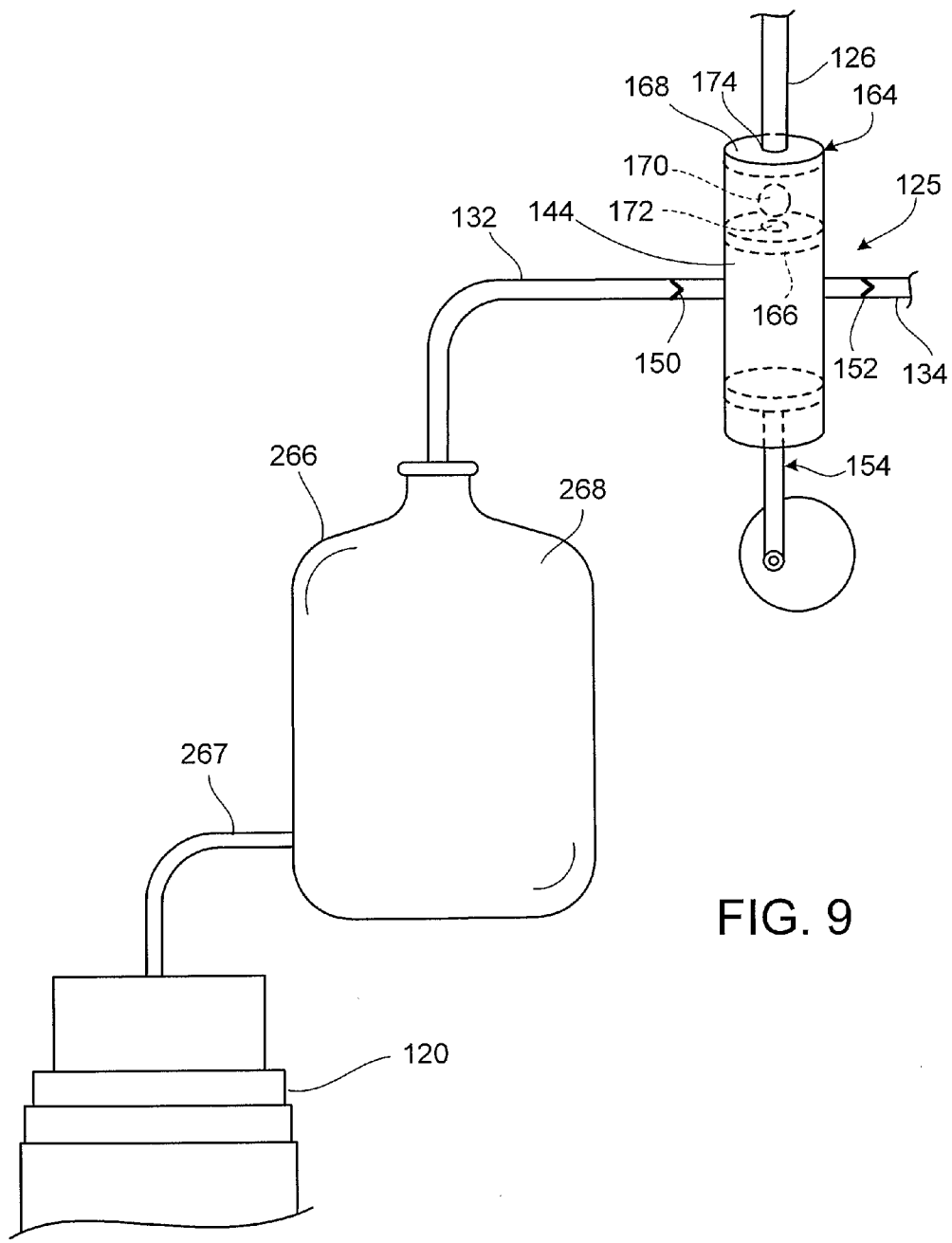
FIG. 9 illustrates the venting device of FIGS. 2 and 3 connected to a dialysate reservoir in a manner such that dialysate can be pumped from the dialysate reservoir through the dialysate circuit by operating a piston pump connected to the venting device.

While the venting devices above have been described as being directly connected to a fluid line exiting the sorbent device 120 (i.e., the fluid inlet line 132), in some implementations, as shown in FIG. 9, a dialysate reservoir 266 is positioned between the venting device 125 and the sorbent device 120. A fluid line 267 connects the sorbent device 120 to the dialysate reservoir 266, and the inlet line 132 of the venting device 125 connects the venting device 125 to the dialysate reservoir 266. More specifically, the inlet line 232 is connected to a port in a top region of the dialysate reservoir 266. The dialysate reservoir 266 is a flexible container (e.g., a flexible bag) that can generally conform to the volume of dialysate within a chamber 268 formed by the container. The flexible container can, for example, be formed of any of various flexible materials, such as polyvinyl chloride (PVC), polyethylene, and/or polypropylene. In certain implementations, the flexible container can hold about 50 milliliters to about 100 milliliters of dialysate.

During use, the dialysate reservoir 266 is filled with dialysate, and the venting device 125 is used to draw the dialysate into the fluid chamber 144 of the venting device 125 from the dialysate reservoir 266. The dialysate is then forced out of the fluid chamber 144 via the fluid outlet line 134 to the downstream components of the dialysate circuit, including the conductivity meter 145. Any gas contained in the dialysate entering the dialysate reservoir 266 from the sorbent device 120 tends to collect in the top region of the dialysate reservoir 266. Because the inlet line 132 of the venting device 125 is connected to the port in the top region of the dialysate reservoir 266, the venting device 125 can remove any gas present in the dialysate reservoir 266 prior to removing the dialysate. In certain cases the volume of gas in the dialysate reservoir 266 may exceed the fluid volume that the venting device 125 is capable of removing in a single piston stroke. In such cases, the initial stroke or strokes of the piston will remove only gas from the dialysate reservoir 266. As the gas is passed through the venting device 125 to the vented bag 180 via the venting line 126, the resulting pressure within the fluid chamber 144 of the venting device 125 is insufficient to overcome the resistance of the outlet check valve 152. As a result, the gas exits the venting device 125 via the apertures 172, 174 in the seats 166, 168 of the ball valve assembly 164 only. As the gas is removed from the dialysate reservoir 266, the dialysate reservoir 266 collapses to conform to the remaining volume of dialysate and gas in the chamber 268. After removing the gas from the chamber 268, the dialysate level reaches the port to which the inlet line 132 of the venting device 125 is connected. As a result, subsequent piston strokes will cause the dialysate to be drawn into the fluid chamber 144 of the venting device 125 and then to be expelled from the fluid chamber 144 of the venting device 125. The use of the dialysate reservoir 266 with the venting device 125 can help to ensure that a sufficient volume of dialysate is readily available throughout treatment.

Figure 10:
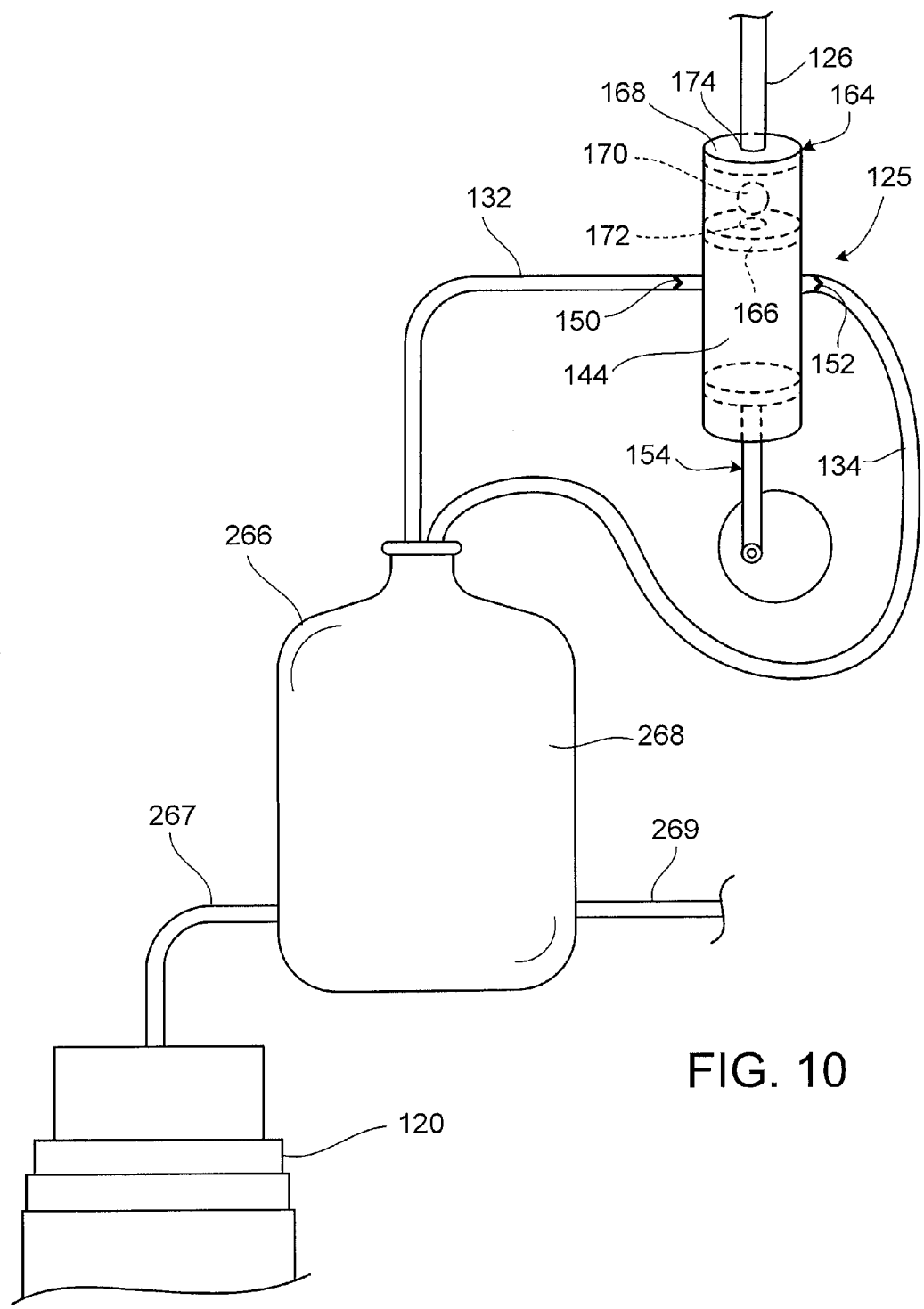
FIG. 10 illustrates the venting device of FIGS. 2 and 3 connected to a dialysate reservoir in a manner such that dialysate can be pumped from the dialysate reservoir through the venting device and then returned to the dialysate reservoir.

In some implementations, as shown in FIG. 10, both the inlet line 132 and the outlet line 134 of the venting device 125 are connected to ports in the top region of the dialysate reservoir 266. In addition, unlike the implementation illustrated in FIG. 9, an outlet line is connected to the dialysate reservoir 266. The outlet line 269 connects the dialysate reservoir 266 to the remainder of the dialysate circuit such that dialysate exiting the dialysate reservoir 266 via the outlet line 269 is directed through the conductivity meter 145 to the dialyzer 135 and then recirculated back through the sorbent device 120 and into the dialysate reservoir 266. In some implementations, it is desirable to pump dialysate through the dialysate circuit at a rate that is faster than the venting device 125 is capable of achieving. The arrangement illustrated in FIG. 10 allows the dialysate to be pumped into and out of the dialysate reservoir 266 at a rate that is generally independent of the pumping capacity of the venting device 125. The venting device 125 in this implementation need only be operated at a rate sufficient to keep the dialysate reservoir 266 substantially free of gases. As the venting device 125 is operated, any gas that has collected in the top region of the dialysate reservoir 266 is drawn into the fluid chamber 144 of the venting device 125 and then expelled to atmosphere via the venting line 126 and vented bag 180. In the event that the volume of gas contained in the dialysate reservoir 266 is less than the volume of the fluid chamber 144 of the venting device 125, both gas and dialysate will be drawn into the fluid chamber 144 as the piston 154 reciprocates. The dialysate that is drawn into the fluid chamber 144 will simply be routed back to the dialysate reservoir 266 via the fluid outlet line 134 during the upstroke of the piston 154. By dedicating the venting device 125 to removing air from the dialysate reservoir 266, rather than both removing air from the dialysate and pumping the dialysate through the dialysate circuit, increased pumping rates can be used.

While the flexible container has been described as being used in conjunction with the venting device 125, it should be understood that the flexible container can alternatively be used with any of the various other venting devices described herein.

While the metering of the infusate into the dialysate has been described as being controlled based on the detected flow rate of the dialysate through the dialysate circuit, in certain implementations, the metering of the infusate into the dialysate is controlled based on conductivity readings of the conductivity sensor 145. In such embodiments, the removal of gas from the dialysate by the venting device 125 can help to ensure that the infusate is delivered into the dialysate at a desired rate and that a desired overall volume of infusate is delivered to the dialysate.

In some implementations, the module 105 alternatively or additionally includes conductivity meters positioned slightly upstream of the sodium chloride container 138 and/or slightly upstream of the infusate solution container 136. These conductivity meters can be used to control the amounts of sodium chloride solution and/or infusate solution delivered to the fluid passing through the fluid outlet line 134. Removing gas from the dialysate prior to measuring the conductivity of the dialysate can improve the accuracy with which the sodium and infusate levels in the dialysate can be predicted based on the conductivity readings, and can thus help to ensure that desired amounts of sodium chloride solution and/or infusate solution are delivered to the dialysate passing through the fluid outlet line 134.

While the external components (e.g., the sorbent device 120, the venting device 125, the infusate container 136, the sodium chloride container 138, the bag 180, the dialysate bag 202, the drain container 203, and their associated fluid lines) connected to the module 105 have been described as being disposable, single use disposable components, any of these components can alternatively be reusable. For example, they can be constructed to withstand disinfection techniques, such as chlorine bleach rinses and/or other chemical rinses. During disinfection, the venting line 126 extending from the venting device 125 is used to introduce the chemical rinse into the fluid chamber 144 of the venting device 125. In particular, the fluid chamber 144 is back filled via the venting line 126. Thus, the venting line 126 allows for a relatively easy rinsing process even where it is difficult to introduce chemical rinse into the fluid chamber via the inlet and outlet lines 132 and 134 due to the inlet and outlet check valves 150 and 152.

While the venting line 126 has been described as being connected to the venting device 125 in a manner to transport gases and overflown dialysate to the vented bag 180, in certain implementations, no such venting line is connected to the venting device 125. In such implementations, for example, the venting device 125 can be directly vented to atmosphere via the aperture 174 of the upper seat 168 of the ball valve assembly 164.

While the module 105 has been described as including pumps 244, 246 for moving the infusate solution and the sodium chloride solution from their respective containers to the fluid outlet line 134, other techniques can alternatively or additionally be used. In certain implementations, for example, a vacuum is used to draw the infusate solution and the sodium chloride solution from their respective containers into the fluid outlet line 134. The flow rate of the dialysate within the fluid outlet line 134 can, for example, create a vacuum that draws the solutions into the fluid outlet line 134. In some implementations, venturi tubes are provided along the fluid outlet line 134 at the locations where the lines 137, 139 extending from the infusate solution container 136 and the sodium chloride solution container 138 join the fluid outlet line 134. The venturi tubes can help to ensure that a sufficient vacuum is created to draw the solutions into the fluid outlet line 134 from their respective containers. In implementations, that use a vacuum to draw the solutions from their respective containers, a valve can be provided within the lines leading from the infusate solution container 136 and the sodium chloride solution container 138 to control the flow rates of the infusate solution and the sodium chloride solution into the fluid outlet line 134. These valves can be connected to and controlled by the microprocessor in the module 105.

In other embodiments, the infusate solution and the sodium chloride solution are delivered to the dialysate using a gravity based delivery system. In such implementations, the flow rate of the infusate solution and sodium chloride solution can be controlled using valves.

While the dilution water has been described as being injected into the dialysate exiting the hemodialysis machine, in some implementations, the dilution water is injected into dialysate exiting the module 105 and entering the hemodialysis machine 110. The dilution water can, for example, be delivered to the fluid outlet line 134 of the venting device 125. In such implementations, in order to deliver the dilution water to the fluid outlet line 134, the hemodialysis machine 110 can draw the dilution water from the dilution water container 141 and delivers the dilution water to the module 105 where it passes through a fluid line that connects to the fluid line 139 connecting the sodium chloride solution container 138 to the fluid outlet line 134. The dilution water can be metered into the fluid outlet line 134 by activating the pump 246 and opening a valve disposed along the line through which the dilution water is passed. Similarly, the sodium chloride solution can be metered into the fluid outlet line 134 by activating the pump 246 and opening the valve 248.

While the systems described herein have been described as including dialysate recycling modules that are connected to the dialysis machine 110, other arrangements are possible. In some implementations, for example, the various components of the module are incorporated into a single dialysis machine.

In some implementations, a venting device is incorporated into a dialysate component carrier (sometimes referred to as a dialysate component cassette) that is configured to cooperate with various internal components (e.g., pumps, sensors, etc.) of a dialysis machine. For example, referring to FIGS. 11 and 12, a hemodialysis system 300 includes a hemodialysis machine 302 having a top module 304 that rests on a bottom module 306. A dialysate component carrier 308 (shown in FIG. 12) is contained within a drawer 310 of the bottom module 306. Various dialysate lines and components, including a venting device 312, are connected to a base 314 of the dialysate component carrier 308. Various fluid lines of the blood component carrier 308 are connected to the dialyzer 135, the sorbent device 120, and a dialysate reservoir 316 to form a dialysate circuit through which dialysate is recirculated during treatment. Additional fluid lines of the dialysate component carrier are connected to a drain container 318 to allow dialysate to be removed from the dialysate circuit and transported to the drain container 318 for disposal. In addition, fluid lines of the dialysate component carrier are connected to a dilution water container 320, a sodium chloride container 322, and an infusate container 324 to allow dilution water, sodium chloride solution, and infusate solution, respectively, to be delivered to the dialysate circuit.

Figure 13:
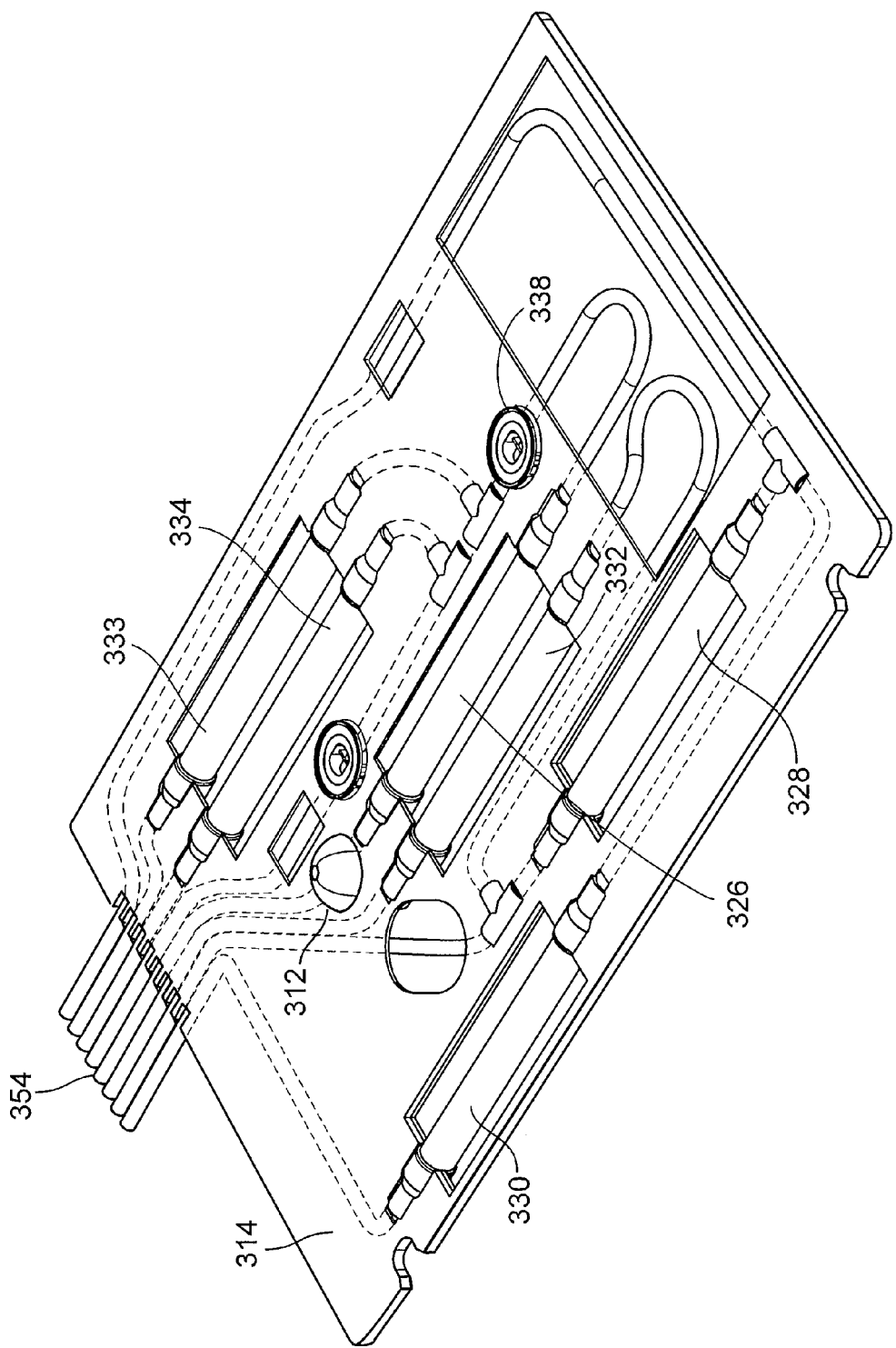
FIG. 13 is a perspective view of the dialysate component carrier of the hemodialysis system of FIG. 11.

Referring to FIG. 13, six pump lines (i.e., a dialyzer inlet pump line 326, a dialyzer outlet pump line 328, an ultrafiltrate pump line 330, a dilution water pump line 332, a sodium chloride solution pump line 333, and an infusate pump line 334) are positioned within apertures formed in the base 314 of the dialysate component carrier 308. The pump line segments cooperate with peristaltic pumps inside the bottom module 306 of the dialysis machine 302 to pump dialysate and other fluids through the dialysate circuit. Additional apertures are also provided in the base 314 of the blood component carrier 308 to permit other instruments (e.g., sensors, heaters, etc.) in the bottom module 306 to access the various fluid lines of the blood component carrier 308 via the apertures. A pressure sensor capsule 336 and an ammonium sensor capsule 338 are positioned in apertures formed in the base 314 of the dialysate component carrier 308 and are arranged to cooperate with a pressure sensor and an ammonium sensor, respectively, located in the bottom module 306 of the hemodialysis machine 302.

Figure 14:
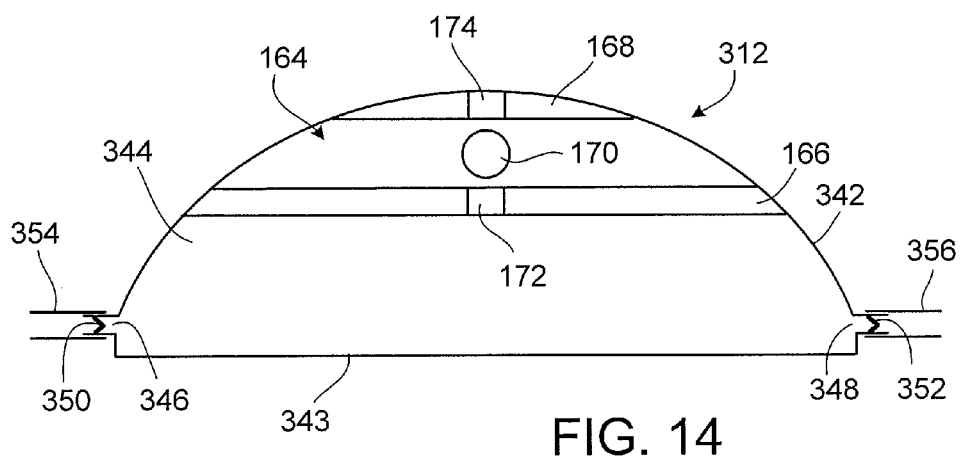
FIG. 14 is a schematic cross-sectional view of the venting device of the dialysate component carrier of FIG. 13.

The venting device 312 is also secured within an aperture formed in the base 314. The venting device 312 has a similar construction to those venting devices described above. As shown in FIG. 14, which is a cross-sectional view of the venting device 312, the venting device 312 includes a relatively rigid hemispherical housing 342 and a flexible membrane 343 secured to the bottom annular surface of the housing 342. The flexible membrane 343 covers a bottom opening in the housing 342. The housing 342 further defines an inlet port and an outlet port 346 and 348 in which an inlet check valve 350 and an outlet check valve 352 are respectively positioned. Inlet and outlet lines 354, 356 are connected to the inlet and outlet ports 346, 348. The ball valve assembly 164 is disposed in the top region of the fluid chamber.

The housing 342 can be formed of any of various rigid materials, including, for example, polyethylene terephthalate (PETE), polyvinyl chloride (PVC), high density polyethylene (HDPE), low density polyethylene (LDPE), polypropylene, and/or polystyrene. The membrane 343 can be formed of any of various resilient materials, including, for example, silicone, polyvinyl chloride (PVC), and/or polyethylene.

The venting device 312 is typically formed separately from the base 314 of the dialysate component carrier 308 and then permanently attached to the base 314. The venting device 312 can, for example, be adhesively bonded and/or thermally bonded to the base 314. The venting device 312 can alternatively be releasably attached to the base 314. In certain implementations, for example, the venting device 312 is designed to snap fit into an aperture formed in the base 314 of the dialysate component carrier 308.

Figure 11:
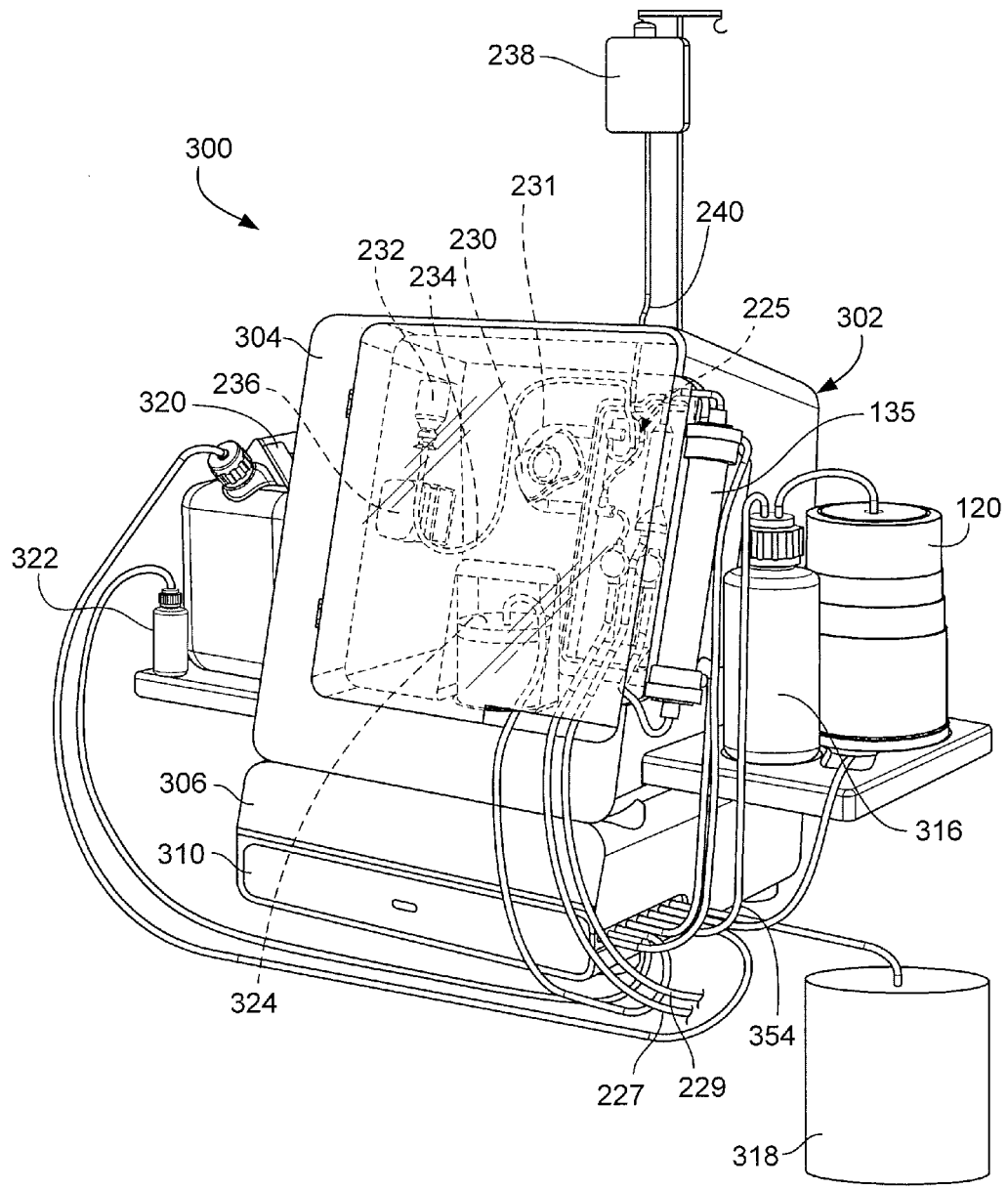
FIG. 11 is a perspective view of a hemodialysis system.
Figure 12:
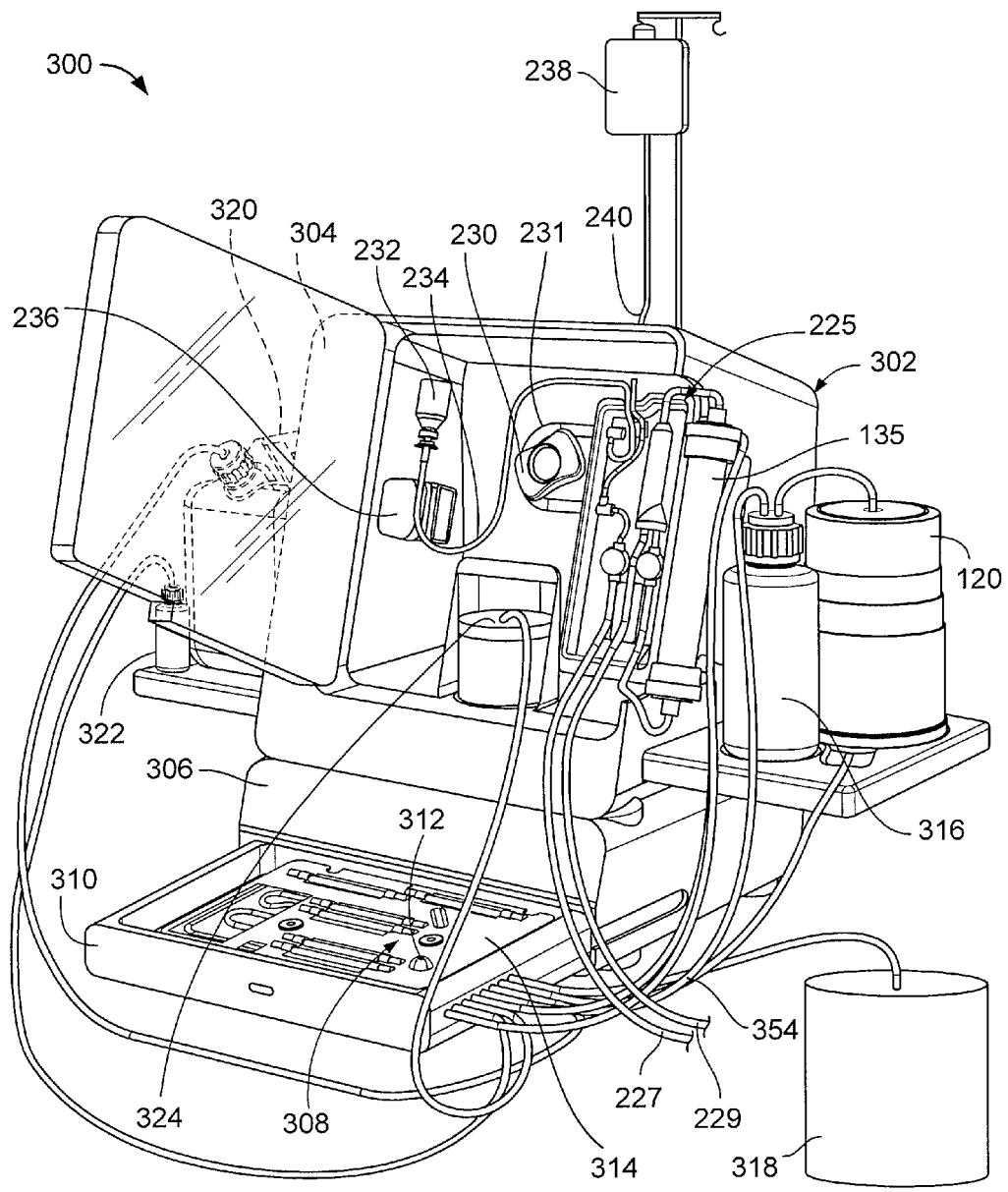
FIG. 12 is a perspective view of the hemodialysis system of FIG. 11 with a door open to expose a blood component set and with a drawer open to expose a dialysate component carrier, which includes a venting device.

As shown in FIGS. 11-13, during use, the end region of the fluid inlet line 354 opposite the venting device 312 is connected to the dialysate reservoir 316, and the end region of the fluid outlet line 356 opposite the venting device 312 is connected to the dialyzer inlet pump line 326. The housing 342 and the membrane 343 together form a fluid chamber 344. When the drawer 310 is closed, the dialysate component carrier 308 and its components are mechanically lifted to compress the dialysate component carrier 308 and its components against an instrument bearing surface of the bottom module 306.

Figure 15:
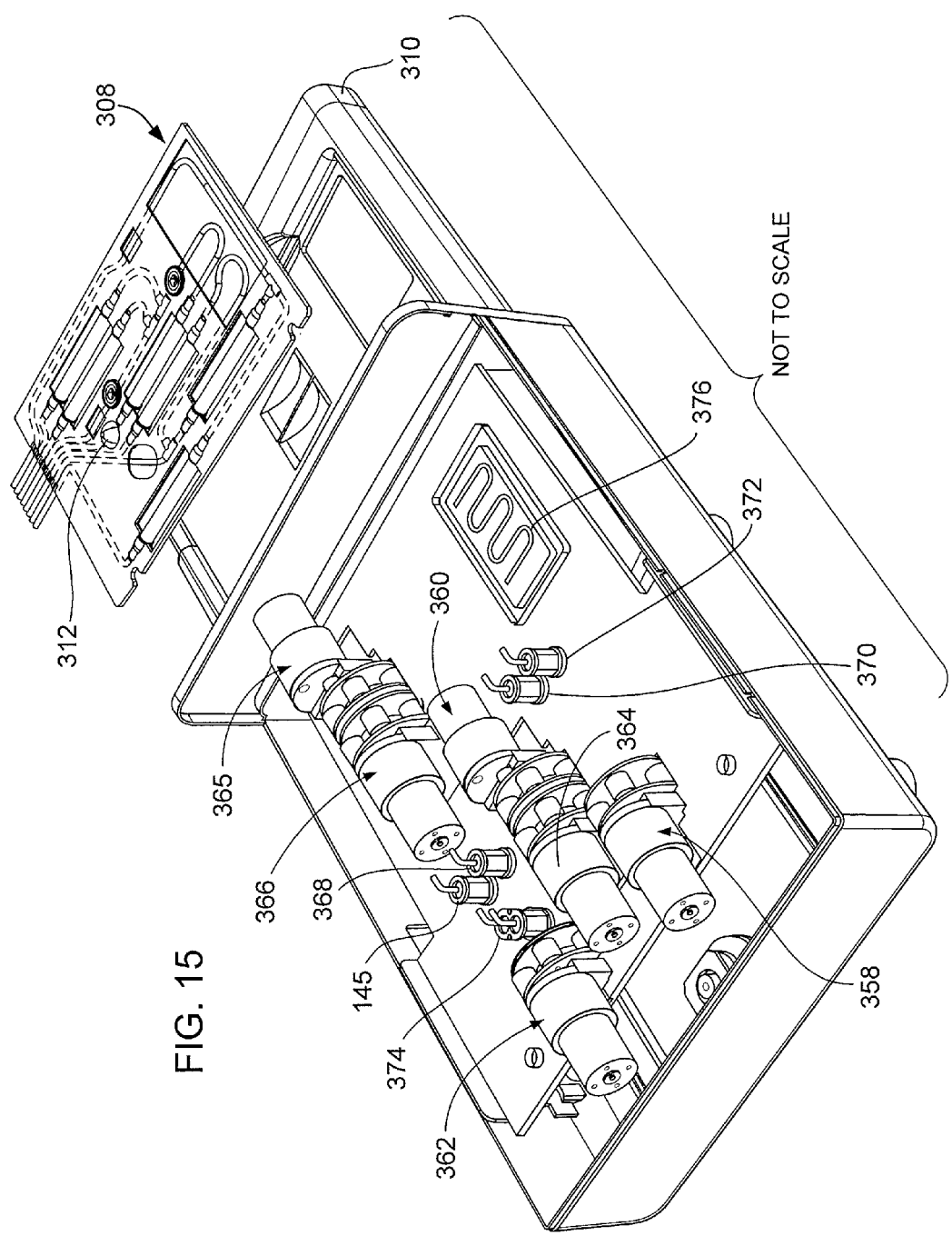
FIG. 15 is a cut-away view of a portion of the hemodialysis system of FIG. 11 with the drawer open and various internal components of the hemodialysis system exposed.

FIG. 15 is a cut away view of the bottom module 306, which shows a dialyzer outlet pump 358, a dialyzer inlet pump 360, an ultrafiltrate pump 362, a dilution water pump 364, a sodium chloride solution pump 365, an infusate pump 366, the conductivity meter 145, an ammonium sensor 368, a blood leak detector 370, a pressure sensor 372, a temperature sensor 374, and a heater 376 positioned above the drawer cavity of the bottom module 306. Each of the pumps 358, 360, 362, 364, 365, 366 is a peristaltic pump that includes multiple rolling members positioned about the circumference of a rotatable frame. When pump lines 326, 328, 330, 332, 333, 334 secured to the base 314 of the dialysate component carrier 308 are pressed against the rolling members of the pumps 358, 360, 362, 364, 365, 366, the pump lines 326, 328, 330, 332, 333, 334 deflect into recesses or raceways formed along the bottom surface of the drawer 310. As the pump frames are rotated, the rolling members apply pressure to the associated pump lines and force dialysate and other solutions through the pump lines and the various other dialysate lines of the system.

The conductivity meter 145, the ammonium sensor 368, the blood leak detector 370, the pressure sensor 372, and the temperature sensor 374 can be any of various devices capable of detecting the conductivity, ammonium level, blood, pressure, and temperature, respectively, of dialysate passing through the lines associated with those instruments.

The heater 376 is capable of raising the temperature of the dialysate flowing through the dialysate circuit to a desired temperature (e.g., about body temperature) and then maintaining the flowing fluid within an acceptable temperature range.

Figure 16:
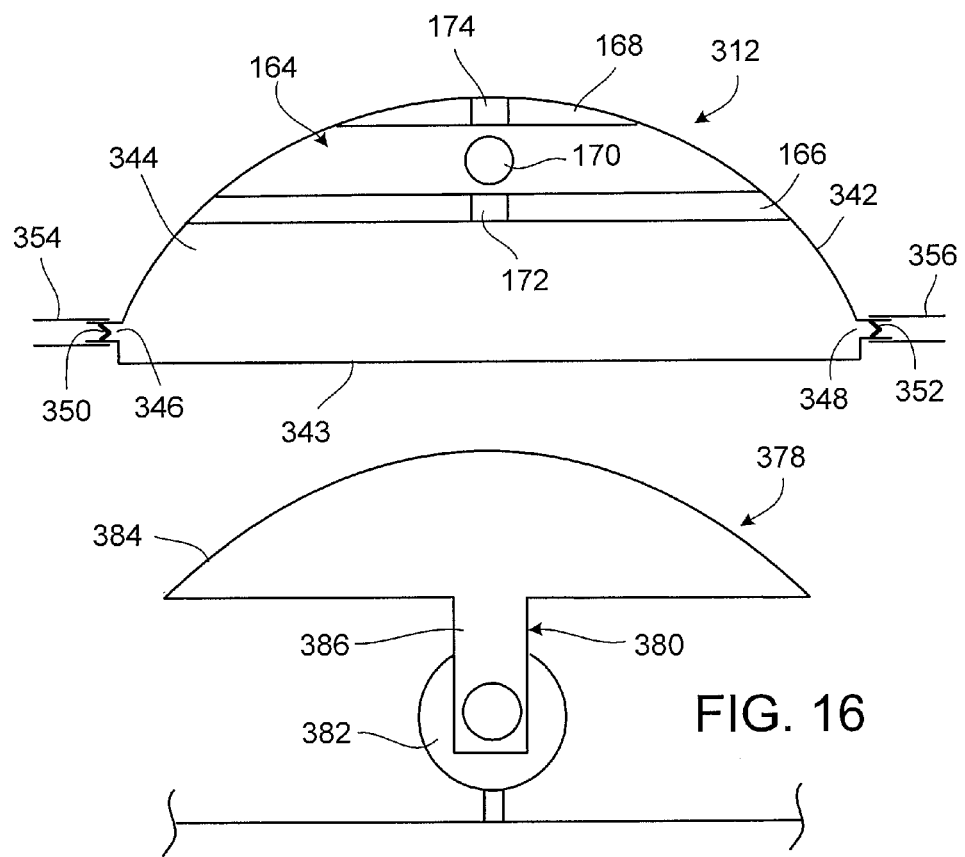
FIG. 16 illustrates the venting device of the dialysate component carrier of FIG. 13 being used in combination with a piston pump.

As shown in FIG. 16, a piston pump 378 extends from a bottom surface of the bottom module 306. Similar to the piston pumps described above, the piston pump 378 includes a piston 380 secured to a rotatable disk 382 that reciprocates the piston 380 in the vertical direction when the disk 382 is rotated. The piston 380 includes a piston head 384 secured to a piston shaft 386, which is secured to the rotatable disk 382. The piston pump 378 is positioned so that the piston head 384 aligns with the membrane 343 of the venting device 312 when the drawer 310 of the bottom module 306 is fully closed, as shown in FIG. 16. During use, the piston head 384 is secured to the membrane 343 to ensure that the membrane 343 retracts along with the piston head 384 to alter the volume of the fluid chamber 344 of the venting device 312. The piston 380 can, for example, include a vacuum channel that extends along the piston shaft 386 and through the piston head 384 and is connected to a vacuum source within the dialysis machine 302 such that vacuum pressure within the channel holds the membrane 343 against the piston head 384. Alternatively, the piston head 384 can be adhesively attached to the membrane 343 during use. The piston 380 can deform the flexible membrane 343 of the venting device 312 during use to change the volume of the fluid chamber 344, and thus change the pressure within the fluid chamber 344. The piston pump 378 can, therefore, be used in a manner similar to the piston pumps described above to draw dialysate into the fluid chamber via the fluid inlet line 354, vent gas from the fluid chamber 344, and then force the dialysate out of the fluid chamber 344 via the fluid outlet line 356.

Figure 17:
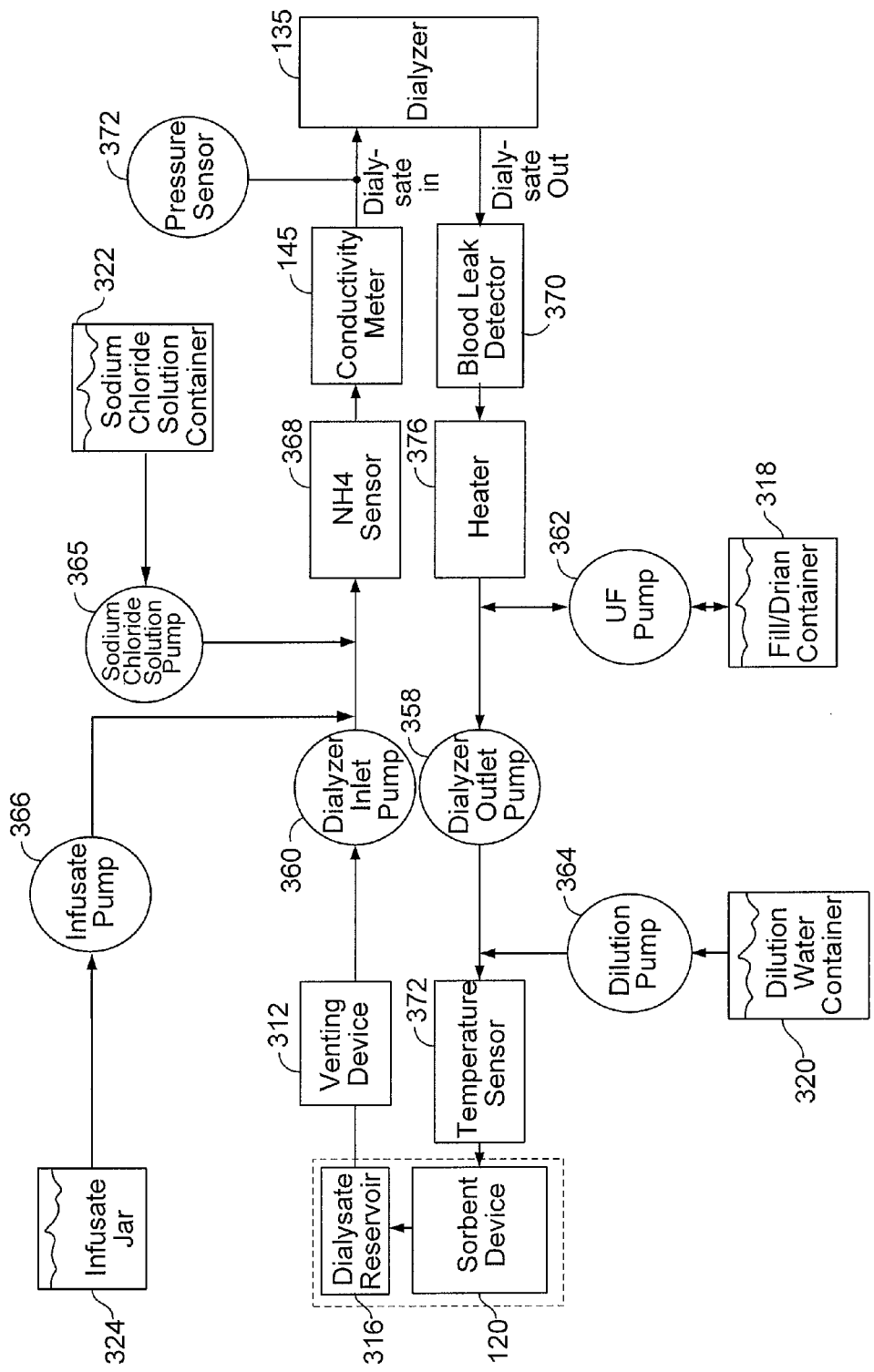
FIG. 17 is a schematic of fluid flow through a dialysate circuit of the hemodialysis system of FIG. 11 during hemodialysis.

Referring to FIG. 17, during use, dialysate is circulated through the dialysate circuit formed by the dialysate lines, the dialyzer 135, the sorbent device 120, the dialysate reservoir 316, the venting device 312, and the various other dialysate components connected to the dialysate component carrier 308. The dialysate passes through the dialyzer 135 along with the blood to remove toxins from the blood. The spent dialysate exiting the dialyzer 135 is routed to the sorbent device 120 where the toxins, including urea, are stripped from the spent dialysate. The recycled dialysate exiting the sorbent device 120 is passed through the venting device 312, which vents gas from the recycled dialysate. Infusate solution and/or sodium chloride solution can be introduced to the recycled dialysate after the recycled dialysate exits the venting device 312 to ensure that the recycled dialysate has a desired concentration of magnesium, calcium, potassium, and sodium. Similarly, dilution water can be introduced into the dialysate before the dialysate enters the sorbent device 120. As discussed above, the amount of infusate solution, sodium chloride solution, and/or dilution water added to the dialysate can be controlled based on the readings of the conductivity meter 145. By removing gas from the dialysate, the venting device 312 improves the ability of the system to determine desired amounts of infusate solution, sodium chloride solution, and/or dilution water to add to the dialysate. The recycled dialysate is then re-circulated through the dialysate circuit and re-used to filter blood of the patient.

Additional information related to dialysis systems and methods that use dialysate component carriers of the type discussed above can be found in U.S. Patent Application 61/231,220, filed on Aug. 4, 2009 and entitled "Dialysis Systems, Components, and Methods," which is incorporated by reference herein.

While the venting device 312 has been described as venting gas directly to atmosphere, a venting line can alternatively be connected to the vent (e.g., opening) of the venting device 312 in a manner such that gases and liquids escaping the venting device 312 via the vent can be collected in a vented bag or container.

While the hemodialysis system 300 is configured so that dilution water is introduced into the dialysate before the dialysate reaches the sorbent device 120 and sodium chloride solution is introduced into the dialysate after the dialysate exits the sorbent device 120, other arrangements are possible. In certain implementations, for example, the system is configured such that the dilution water and sodium chloride solution are both introduced to the dialysate before the dialysate enters the sorbent device 120. The pumps, pump lines, and line segments associated with the delivery of the dilution water container 320 and the sodium chloride solution container 322 can, for example, be reconfigured to deliver the dilution water and sodium chloride solution to the flowing dialysate. Alternatively, lines extending from the dilution water container 320 and the sodium chloride solution container 322 can be connected to a common line via a actuated three-way valve. The common line in this example can be connected at its opposite end to the pump line 332 in FIG. 13.

The three-way valve can be actuated in a manner so that as the pump associated with the pump line 332 is operated dilution water, sodium chloride solution, or no liquid is delivered to the dialysate via the common line.

While the systems described above are configured to deliver dilution water (e.g., tap water) to dialysate before the dialysate enters the sorbent device 120 (i.e., at a pre-sorbent device location), any of the systems described herein can alternatively or additionally be configured so that dilution water is introduced to dialysate after the dialysate exits the sorbent device 120 (i.e., at a post-sorbent device location). In such implementations, the dilution water would not pass through the sorbent device 120 before being delivered to the dialyzer 135. Therefore, the dilution water in such implementations would typically be a pre-filtered or purified water, such as AAMI water.

While the piston pumps above have been described as using a rotatable disk to reciprocate the piston, any of various other techniques of reciprocating the piston can be used. The piston pumps can, for example, include a stepper motor to drive the piston. Alternatively, hydraulically or pneumatically driven piston pumps can be used.

In certain implementations, the reciprocating action of the piston is produced by a rotational source, a linear motor, a solenoid, a ball screw, or other pulsatile flow sources.

While the systems described above use the sorbent device 120 to remove toxins from the spent dialysate, other types of devices can alternatively or additionally be used to remove toxins from the spent dialysate. The venting devices described herein can beneficially remove gases from the dialysate exiting any such devices.

While the venting devices have been described as being used in hemodialysis systems adapted to recycle spent dialysate, the venting devices can similarly be used in traditional, single path hemodialysis systems that simply dispose of the spent dialysate. The venting devices can, for example, advantageously remove any gases, such as air, that might enter the dialysate circuit of such systems (e.g., via loose fittings, connectors, etc.) during the hemodialysis treatment.

While the venting devices have been described as being part of the dialysate component set to remove gases from the dialysate, the venting devices can alternatively or additionally be used in the blood component set to remove gases from the blood.

While the venting devices have been described as being used in hemodialysis systems, the venting devices can similarly be used in other types of dialysis systems, such as peritoneal dialysis systems. The venting devices described herein could also be used in any of various other types of medical systems, such as peritoneal drug delivery devices, cancer therapy infusion devices, drug infusion devices, and surgery suction devices.

Other implementations are within the scope of the following claims.

What is claimed is:

1. A dialysis system, comprising:
    a dialyzer;
    a fluid inlet line;
    a venting device comprising
        a housing defining a fluid chamber in fluid communication with the fluid inlet line, and
        a valve member disposed above the fluid chamber between a lower seat and an upper seat, the lower seat defining an aperture, and the upper seat defining an aperture;
    a fluid outlet line in fluid communication with the venting device such that fluid exiting the venting device flows through the fluid outlet line; and
    a pump comprising a member disposed within the fluid chamber, the pump being operable to draw fluid into the fluid chamber via the fluid inlet line using negative pressure and to force fluid out of the fluid chamber via the fluid outlet line using positive pressure.

2. The dialysis system of claim 1, further comprising a sorbent device in fluid communication with the fluid inlet line such that fluid flows through the fluid inlet line after the fluid exits the sorbent device.

3. The dialysis system of claim 2, further comprising a sensor positioned along the fluid outlet line, the sensor configured to measure one or more parameters of fluid flowing through the fluid outlet line.

4. The dialysis system of claim 3, wherein the venting device is positioned between the sorbent device and the sensor.

5. The dialysis system of claim 3, wherein the sensor is a conductivity sensor configured to measure a conductivity of fluid flowing through the fluid outlet line.

6. The dialysis system of claim 1, wherein the dialyzer is in fluid communication with the fluid outlet line such that fluid flows through the dialyzer after exiting the venting device.

7. The dialysis system of claim 1, further comprising an inlet check valve positioned along the fluid inlet line and an outlet check valve positioned along the fluid outlet line.

8. The dialysis system of claim 7, wherein the inlet check valve has a greater flow resistance than the valve member such that fluid more easily passes through the apertures in the upper and lower seats then through the inlet check valve when negative pressure is applied to the fluid chamber.

9. The dialysis system of claim 7, wherein the outlet check valve has a greater flow resistance than the valve member such that fluid more easily passes through the apertures in the upper and lower seats then through the outlet check valve when positive pressure is applied to the fluid chamber.

10. The dialysis system of claim 1, wherein the venting device is configured so that the fluid chamber is in communication with atmospheric air when the valve member is not seated against the lower seat or the upper seat such that gases can be vented from the fluid chamber to the atmospheric air via the apertures.

11. The dialysis system of claim 1, wherein the housing of the venting device comprises a membrane that can be deformed to alter the volume of the fluid chamber.

12. The dialysis system of claim 11, wherein the pump comprises a piston configured to deform the membrane.

13. The dialysis system of claim 11, wherein the dialysis system comprises a dialysate component carrier having a base, and the venting device is attached to the base of the dialysate component carrier.

14. The dialysis system of claim 1, further comprising a second venting device, wherein the venting devices are arranged such that fluid can be drawn into one of the venting devices as fluid is being expelled from the other venting device.

15. The dialysis system of claim 1, further comprising a fluid reservoir positioned between the sorbent device and the venting device, the fluid reservoir being in fluid communication with both the sorbent device and the venting device.

16. The dialysis system of claim 15, wherein the fluid reservoir comprises a collapsible container.

17. The dialysis system of claim 16, wherein the fluid inlet line is connected to a port formed in a top region of the flexible container.

18. The dialysis system of claim 15, wherein the fluid reservoir is sized to contain about 50 milliliters to about 100 milliliters of fluid.

19. The dialysis system of claim 1, wherein the valve member is a ball.

20. The dialysis system of claim 19, wherein the ball is buoyant.

21. The dialysis system of claim 20, wherein the ball is hollow.

22. The dialysis system of claim 1, wherein the pump is a piston pump.

23. The dialysis system of claim 1, wherein the dialysis system is a hemodialysis system.

24. The dialysis system of claim 1, wherein the dialysis system is a peritoneal dialysis system.

25. The dialysis system of claim 1, wherein the dialysis system is configured so that dialysate flows through the venting device during use.

26. The dialysis system of claim 1, wherein the dialysis system is configured so that blood flows through the venting device during use.

27. The venting method of claim 1, wherein the member is a reciprocatable member that is disposed within the fluid chamber.

28. A dialysis system, comprising:
a dialyzer; and
a venting device comprising:
    a housing defining a chamber, a liquid inlet port, and a liquid outlet port;
    a reciprocatable member disposed within the housing and configured to change a pressure within the chamber as the reciprocatable member reciprocates; and
    a buoyant valve member disposed above the chamber between a lower seat and an upper seat, the lower seat defining an aperture, and the upper seat defining an aperture,
    wherein the buoyant member is configured to seal the aperture of the lower seat when the reciprocatable member is moved in a first direction and to seal the aperture of the upper seat when the reciprocatable member is moved in a second direction.

29. A venting method, comprising:
drawing dialysis fluid into a fluid chamber of a venting device by applying vacuum pressure to the fluid chamber, wherein gas is released from the dialysis fluid within the fluid chamber;
forcing the gas out of the fluid chamber by applying positive pressure to the fluid chamber for a first period of time; and then
forcing the dialysis fluid out of the fluid chamber by continuing to apply positive pressure to the fluid chamber for a second period of time.

30. The venting method of claim 29, wherein a valve member is positioned above the fluid chamber between a lower seat and an upper seat, the lower seat defining an aperture, and the upper seat defining an aperture.

31. The venting method of claim 30, wherein drawing dialysis fluid into the fluid chamber comprises drawing the valve member against the lower seat to seal the aperture defined by the lower seat.

32. The venting method of claim 30, wherein, prior to forcing the dialysis fluid out of the fluid chamber, the valve member is forced against the upper seat to seal the aperture defined in the upper seat.

33. The venting method of claim 29, wherein the vacuum pressure is applied to the fluid chamber by moving a reciprocatable member connected to the venting device in a first direction, and the positive pressure is applied to the fluid chamber by moving the reciprocatable member connected to the venting device in a second direction opposite the first direction.

34. The venting method of claim 29, wherein the dialysis fluid is drawn into fluid chamber from a dialysis fluid reservoir, the dialysis fluid reservoir being sized to contain a larger volume of fluid than the fluid chamber.

* * * * *

UNITED STATES PATENT AND TRADEMARK OFFICE
CERTIFICATE OF CORRECTION

PATENT NO. : 8,425,780 B2  
APPLICATION NO. : 12/722061  
DATED : April 23, 2013  
INVENTOR(S) : Michael James Beiriger Page 1 of 1

It is certified that error appears in the above-identified patent and that said Letters Patent is hereby corrected as shown below:

In the Claims:

Column 23, line 22 (Claim 27, line 22) delete "venting method" and insert --dialysis system--.

Signed and Sealed this  
Twenty-third Day of July, 2013

Teresa Stanek Rea  
*Acting Director of the United States Patent and Trademark Office*